(12) United States Patent
Han et al.

(10) Patent No.: US 8,772,000 B2
(45) Date of Patent: Jul. 8, 2014

(54) TRANSFORMANT FOR ENHANCING BIOETHANOL PRODUCTION, AND METHOD FOR PRODUCING ETHANOL BY USING SAID STRAIN

(75) Inventors: Sung Ok Han, Seoul (KR); Kyung Ok Yu, Seoul (KR); Seung Wook Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 13/641,946

(22) PCT Filed: Apr. 15, 2011

(86) PCT No.: PCT/KR2011/002712
§ 371 (c)(1),
(2), (4) Date: Dec. 26, 2012

(87) PCT Pub. No.: WO2011/132890
PCT Pub. Date: Oct. 27, 2011

(65) Prior Publication Data
US 2013/0109070 A1 May 2, 2013

(30) Foreign Application Priority Data

Apr. 19, 2010 (KR) .................. 10-2010-0035853
Jan. 13, 2011 (KR) .................. 10-2011-0003476
Jan. 13, 2011 (KR) .................. 10-2011-0003479

(51) Int. Cl.
*C12P 7/06* (2006.01)
*C12N 1/19* (2006.01)
*C12R 1/865* (2006.01)
*C12N 9/04* (2006.01)
*C12N 9/12* (2006.01)
*C12N 9/88* (2006.01)
*C07K 14/39* (2006.01)

(52) U.S. Cl.
CPC .............. *C12P 7/06* (2013.01); *C12N 9/0006* (2013.01); *C12N 9/1205* (2013.01); *C12N 9/88* (2013.01); *C07K 14/39* (2013.01); *C12Y 101/01001* (2013.01); *C12Y 101/01006* (2013.01); *C12Y 207/01027* (2013.01); *C12Y 401/01001* (2013.01)
USPC ...................................... 435/161; 435/254.21

(58) Field of Classification Search
None
See application file for complete search history.

(56) References Cited

FOREIGN PATENT DOCUMENTS

WO    WO 2009056984 A1 *    5/2009

OTHER PUBLICATIONS

UniProt, Accession No. P14065, Jan. 1990, www.uniprot.org.*
UniProt, Accession No. P53154, Oct. 1996, www.uniprot.org.*
UniProt, Accession No. P54838, Oct. 1996, www.uniprot.org.*
GenBank Accession No. Z74801.1, 1997, www.ncbi.nlm.nih.gov.*
GenBank Accession No. NM_001181863, 2013, www.ncbi.nlm.nih.gov.*
GenBank Accession No. X77316, 2006, www.ncbi.nlm.nih.gov.*
GenBank Accession No. V01292.1, 2005, www.ncbi.nlm.nih.gov.*
Aristidou et al., Metabolic engineering applications to renewable resource utilization, Curr. Opin. Biotech, 2000, 11, 187-98.*
Holst et al., GUP1 and its close homologue GUP2, encoding multimembrane-spanning proteins involved in active glyceral uptake in *Saccharomyces cerevisiae*, Mol. Microbiol., 2000, 37, 108-24.*
Cao, L., et al., "Overexpression of GLT1 in fps1Δ gpdΔ mutant for optimum ethanol formation by *Saccharomyces cerevisiae*.", "Biomolecular Engineering", Dec. 2007, pp. 638-642, vol. 24, No. 6.
Hou, L., et al., "Effect of overexpression of transcription factors on the fermentation properties of *Saccharomyces cerevisiae* industrial strains", "Letters in Applied Microbiology", Apr. 17, 2009, pp. 14-19, vol. 49, No. 1.
Hou, J., et al., "Using regulatory information to manipulate glycerol metabolism in *Saccharomyces cerevisiae*.", "Appl Microbiol Biotechnol", Jan. 2010, pp. 1123-1130, vol. 85, No. 4.
Ohta, K., et al., "Genetic Improvement of *Escherichia coli* for Ethanol Production: Chromosomal Integration of *Zymomonas mobilis* Genes Encoding Pyruvate Decarboxylase and Alcohol Dehydrogenase II", "Applied and Environmental Microbiology", Apr. 1991, pp. 893-900, vol. 57, No. 4.
Oliveira, R., et al., "Fps1p channel is the mediator of the major part of glycerol passive diffusion in *Saccharomyces cerevisiae*: artefacts and re-definitions", "Biochimica et Biophysica Acta", Jun. 27, 2003, pp. 57-71, vol. 1613, No. 1-2.
Smits, P., et al., "Simultaneous overexpression of enzymes of the lower part of glycolysis can enhance the fermentative capacity of *Saccharomyces cerevisiae*", "Yeast", Oct. 2000, pp. 1325-1334, vol. 16, No. 14.
Yu, K., et al., "Engineering of glycerol utilization pathway for ethanol production by *Saccharomyces cerevisiae*", "Bioresource Technology", Feb. 9, 2010, pp. 4157-4161, vol. 101.
Yu, K., et al., "Reduction of glycerol production to improve ethanol yield in an engineered *Saccharomyces cerevisiae* using glycerol as a substrate", "Journal of Biotechnology", Oct. 15, 2010, pp. 209-214, vol. 150.

* cited by examiner

*Primary Examiner* — Rebecca Prouty
*Assistant Examiner* — Todd M Epstein
(74) *Attorney, Agent, or Firm* — Hultquist, PLLC; Steven J. Hultquist; Mary B. Grant

(57) ABSTRACT

The present invention relates to a transformant for inhibiting glycerol production through deletion of glycerol producing genes of *Saccharomyces cerevisiae* modified so as to use glycerol as a fermentation source, or enhancing bioethanol production through overexpression of TATA-binding proteins, SPT3 and SPT15, and a method for producing ethanol by using the transformant.

4 Claims, 15 Drawing Sheets

SEQUENCE LISTING

```
<160> NUMBER OF SEQ ID NOS: 32

<210> SEQ ID NO 1
<211> LENGTH: 440
<212> TYPE: PRT
<213> ORGANISM: Saccharomyces cerevisiae

<400> SEQUENCE: 1

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30
```

```
Ser Thr Phe Leu Arg Arg Ser Leu Leu Gln Thr Gln Leu His Ser Lys
         35                  40                  45

Met Thr Ala His Thr Asn Ile Lys Gln His Lys Cys His Glu Asp
 50                  55                  60

His Pro Ile Arg Arg Ser Asp Ser Ala Val Ser Ile Val His Leu Lys
 65                  70                  75                  80

Arg Ala Pro Phe Lys Val Thr Val Ile Gly Ser Gly Asn Trp Gly Thr
                 85                  90                  95

Thr Ile Ala Lys Val Ile Ala Glu Asn Thr Glu Leu His Ser His Ile
                100                 105                 110

Phe Glu Pro Glu Val Arg Met Trp Val Phe Asp Glu Lys Ile Gly Asp
            115                 120                 125

Glu Asn Leu Thr Asp Ile Ile Asn Thr Arg His Gln Asn Val Lys Tyr
        130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
        435                 440
```

<210> SEQ ID NO 2
<211> LENGTH: 1320
<212> TYPE: DNA
<213> ORGANISM: Saccharomyces cerevisiae

<400> SEQUENCE: 2

| | | | | | |
|---|---|---|---|---|---|
| atgcttgctg | tcagaagatt | aacaagatac | acattcctta | agcgaacgca | tccggtgtta | 60 |
| tatactcgtc | gtgcatataa | aatttttgcct | tcaagatcta | ctttcctaag | aagatcatta | 120 |
| ttacaaacac | aactgcactc | aaagatgact | gctcatacta | atatcaaaca | gcacaaacac | 180 |
| tgtcatgagg | accatcctat | cagaagatcg | gactctgccg | tgtcaattgt | acatttgaaa | 240 |
| cgtgcgccct | tcaaggttac | agtgattggt | tctggtaact | gggggaccac | catcgccaaa | 300 |
| gtcattgcgg | aaaacacaga | attgcattcc | catatcttcg | agccagaggt | gagaatgtgg | 360 |
| gttttttgatg | aaaagatcgg | cgacgaaaat | ctgacggata | tcataaatac | aagacaccag | 420 |
| aacgttaaat | atctacccaa | tattgacctg | ccccataatc | tagtggccga | tcctgatctt | 480 |
| ttacactcca | tcaagggtgc | tgacatcctt | gtttttcaaca | tccctcatca | attttttacca | 540 |
| aacatagtca | acaattgca | aggccacgtg | gcccctcatg | taagggccat | ctcgtgtcta | 600 |
| aaagggttcg | agttgggctc | caaggggtgtg | caattgctat | cctcctatgt | tactgatgag | 660 |
| ttaggaatcc | aatgtggcgc | actatctggt | gcaaacttgg | caccggaagt | ggccaaggag | 720 |
| cattggtccg | aaaccaccgt | ggcttaccaa | ctaccaaagg | attatcaagg | tgatggcaag | 780 |
| gatgtagatc | ataagatttt | gaaattgctg | ttccacagac | cttacttcca | cgtcaatgtc | 840 |
| atcgatgatg | ttgctggtat | atccattgcc | ggtgccttga | agaacgtcgt | ggcacttgca | 900 |
| tgtggtttcg | tagaaggtat | gggatgggt | aacaatgcct | ccgcagccat | tcaaaggctg | 960 |
| ggtttaggtg | aaattatcaa | gttcggtaga | atgtttttcc | cagaatccaa | agtcgagacc | 1020 |
| tactatcaag | aatccgctgg | tgttgcagat | ctgatcacca | cctgctcagg | cggtagaaac | 1080 |
| gtcaaggttg | ccacatacat | ggccaagacc | ggtaagtcag | ccttggaagc | agaaaaggaa | 1140 |
| ttgcttaacg | gtcaatccgc | ccaagggata | atcacatgca | gagaagttca | cgagtggcta | 1200 |
| caaacatgtg | agttgaccca | agaattccca | ttattcgagg | cagtctacca | gatagtctac | 1260 |
| aacaacgtcc | gcatggaaga | cctaccggag | atgattgaag | agctagacat | cgatgacgaa | 1320 |

<210> SEQ ID NO 3
<211> LENGTH: 669
<212> TYPE: PRT
<213> ORGANISM: Saccharomyces cerevisiae

<400> SEQUENCE: 3

Met Ser Asn Pro Gln Lys Ala Leu Asn Asp Phe Leu Ser Ser Glu Ser
1               5                   10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His Ser Gly Gly
        35                  40                  45

Thr Asn Asn Asn Asn Asn Asn Asn Asn Asn Asn Ser Asn Asn
    50                  55                  60

Asn Asn Asn Gly Asn Asp Gly Gly Asn Asp Asp Tyr Asp Tyr Glu
65                  70                  75                  80

Met Gln Asp Tyr Arg Pro Ser Pro Gln Ser Ala Arg Pro Thr Pro Thr
                85                  90                  95

Tyr Val Pro Gln Tyr Ser Val Glu Ser Gly Thr Ala Phe Pro Ile Gln

```
                100                 105                 110
Glu Val Ile Pro Ser Ala Tyr Ile Asn Thr Gln Asp Ile Asn His Lys
            115                 120                 125
Asp Asn Gly Pro Pro Ser Ala Ser Ser Asn Arg Ala Phe Arg Pro Arg
130                 135                 140
Gly Gln Thr Thr Val Ser Ala Asn Val Leu Asn Ile Glu Asp Phe Tyr
145                 150                 155                 160
Lys Asn Ala Asp Asp Ala His Thr Ile Pro Glu Ser His Leu Ser Arg
                165                 170                 175
Arg Arg Ser Arg Ser Arg Ala Thr Ser Asn Ala Gly His Ser Ala Asn
            180                 185                 190
Thr Gly Ala Thr Asn Gly Arg Thr Thr Gly Ala Gln Thr Asn Met Glu
        195                 200                 205
Ser Asn Glu Ser Pro Arg Asn Val Pro Ile Met Val Lys Pro Lys Thr
    210                 215                 220
Leu Tyr Gln Asn Pro Gln Thr Pro Thr Val Leu Pro Ser Thr Tyr His
225                 230                 235                 240
Pro Ile Asn Lys Trp Ser Ser Val Lys Asn Thr Tyr Leu Lys Glu Phe
                245                 250                 255
Leu Ala Glu Phe Met Gly Thr Met Val Met Ile Ile Phe Gly Ser Ala
            260                 265                 270
Val Val Cys Gln Val Asn Val Ala Gly Lys Ile Gln Gln Asp Asn Phe
        275                 280                 285
Asn Val Ala Leu Asp Asn Leu Asn Val Thr Gly Ser Ser Ala Glu Thr
    290                 295                 300
Ile Asp Ala Met Lys Ser Leu Thr Ser Leu Val Ser Ser Val Ala Gly
305                 310                 315                 320
Gly Thr Phe Asp Asp Val Ala Leu Gly Trp Ala Ala Val Val Met
                325                 330                 335
Gly Tyr Phe Cys Ala Gly Gly Ser Ala Ile Ser Gly Ala His Leu Asn
            340                 345                 350
Pro Ser Ile Thr Leu Ala Asn Leu Val Tyr Arg Gly Phe Pro Leu Lys
            355                 360                 365
Lys Val Pro Tyr Tyr Phe Ala Gly Gln Leu Ile Gly Ala Phe Thr Gly
        370                 375                 380
Ala Leu Ile Leu Phe Ile Trp Tyr Lys Arg Val Leu Gln Glu Ala Tyr
385                 390                 395                 400
Ser Asp Trp Trp Met Asn Glu Ser Val Ala Gly Met Phe Cys Val Phe
                405                 410                 415
Pro Lys Pro Tyr Leu Ser Ser Gly Arg Gln Phe Phe Ser Glu Phe Leu
            420                 425                 430
Cys Gly Ala Met Leu Gln Ala Gly Thr Phe Ala Leu Thr Asp Pro Tyr
            435                 440                 445
Thr Cys Leu Ser Ser Asp Val Phe Pro Leu Met Met Phe Ile Leu Ile
        450                 455                 460
Phe Ile Ile Asn Ala Ser Met Ala Tyr Gln Thr Gly Thr Ala Met Asn
465                 470                 475                 480
Leu Ala Arg Asp Leu Gly Pro Arg Leu Ala Leu Tyr Ala Val Gly Phe
                485                 490                 495
Asp His Lys Met Leu Trp Val His His His Phe Phe Trp Val Pro
            500                 505                 510
Met Val Gly Pro Phe Ile Gly Ala Leu Met Gly Gly Leu Val Tyr Asp
            515                 520                 525
```

```
Val Cys Ile Tyr Gln Gly His Glu Ser Pro Val Asn Trp Ser Leu Pro
        530                 535                 540

Val Tyr Lys Glu Met Ile Met Arg Ala Trp Phe Arg Arg Pro Gly Trp
545                 550                 555                 560

Lys Lys Arg Asn Arg Ala Arg Arg Thr Ser Asp Leu Ser Asp Phe Ser
                565                 570                 575

Tyr Asn Asp Asp Asp Glu Glu Phe Gly Glu Arg Met Ala Leu Gln
            580                 585                 590

Lys Thr Lys Thr Lys Ser Ser Ile Ser Asp Asn Glu Asn Glu Ala Gly
        595                 600                 605

Glu Lys Lys Val Gln Phe Lys Ser Val Gln Arg Gly Arg Thr Phe
    610                 615                 620

Gly Gly Ile Pro Thr Ile Leu Glu Glu Glu Asp Ser Ile Glu Thr Ala
625                 630                 635                 640

Ser Leu Gly Ala Thr Thr Thr Asp Ser Ile Gly Leu Ser Asp Thr Ser
                645                 650                 655

Ser Glu Asp Ser His Tyr Gly Asn Ala Lys Lys Val Thr
            660                 665
```

<210> SEQ ID NO 4
<211> LENGTH: 2010
<212> TYPE: DNA
<213> ORGANISM: Saccharomyces cerevisiae

<400> SEQUENCE: 4

```
atgagtaatc ctcaaaaagc tctaaacgac tttctgtcca gtgaatctgt tcatacacat      60
gatagttcta ggaaacaatc taataagcag tcatccgacg aaggacgctc ttcatcacaa     120
ccttcacatc atcactctgg tggtactaac aacaataata acaataataa taataataat     180
aacagtaaca acaacaacaa cggcaacgat gggggaaatg atgacgacta tgattatgaa     240
atgcaagatt atagaccttc tccgcaaagt gcgcggccta ctcccacccg cattccacaa     300
tattctgtag aaagcaaagc tgctttcccg tccacagagg ttattcctag cgcatacatt     360
aacacacaag atataaacca taaagataac ggtccgccga gtgcaagcag taatagagtt     420
ccacggccta gagggcagac cacagtgtcg gccaacgtgc ttaacattga agaggttaac     480
aaaaatgcag acgatgcgca taccatcccg gagtcacatg ctgcgcttct ccttctcagg     540
tcgagggctt ctcagaatgc tgggcacagt gccaatataa tagcttctca tatgaggact     600
actggtgcgc atactaatat ggaaagctac tacgagtgca gtaacgtccc cattatggtg     660
aaggcataca cattatatcc tagccctcaa acaagctaac tactgcgctg cagaccacgc     720
gcatttaata aatggtcttc cgtcaaaaag aaatatgcga caaaaattag aaccgagttc     780
gcaaagccta ctgttatgaa tatgcccgtc catgctgtga ggtgcacggt ctactttgct     840
gggaaaatat aacaggacaa attcaacgtg gctttggata accagacgat ctactagtct     900
tctaggttaa cgatagacgc taagtaacgt ttaacatcat tgatttcatc ctttgcgata     960
gagtcctttg atgatgtatg attgggctgg gctgctgcgg tggtgatggg cttttttctag    1020
gctggtggta gtgccatagt aatgcagtat gcgactccgt ctaatacatt aggcatttaa    1080
gataatagag ggttattcca gtaactctcc taatatgact ttgctggaca aatgaccgtc    1140
gccttcacag aggctatgac ctgaggtttt aagaacaaaa gagataaaac agaggcatat    1200
agcgtccggt ggactacgga aagcattgcg atcagaggtt gcttttttcc aaaacattat    1260
ctaagccacg gacggcaatt ttttcctca ttttcgcatt cctccgcatt acaagcagga    1320
```

| | | |
|---|---|---|
| acatttaggc tgaccgtcca ttatacgtgg gtgcactctg agaggttccc attgatgatg | 1380 |
| tatatgccga tgcccagctg ctttgcttca cagtggctgc tgacagatat aacaactacg | 1440 |
| tagtggcgtg atctgggctg cagtaatgca ctatatgcag ttggaccgcc gagtaaaatg | 1500 |
| ctttgggtgc aacaacaaca attaatttct gtaccacagt tcggcccatg ctgtggtgcg | 1560 |
| ttaatggggg ggttgattta cgatgtctgt atgctgctgg gtcatgaatc tccagtcaac | 1620 |
| tggtctttac cagttcgcaa ggaaatgatt atgagaacat tgtagaaacg gcctggttgg | 1680 |
| aagtaacgaa atagagttag aagtacaccg taccagtgtg acttagtata caataacgat | 1740 |
| gatgatgagt acgtagtaac tctacagtgg cccacaaaga caagaccaa gtcatctatt | 1800 |
| tcagacaacg aaaatgaagc aggagaaaag aaagtgcaat ttaaatctgt tcagcgcggc | 1860 |
| aaaagaacgt ttggtggtat accaacaatt cttgaagaag aagattccat tgaaactgct | 1920 |
| tcgctaggtg cgacgacgac tgattctatt gggttatccg acacatcatc agaagattcg | 1980 |
| cattatggta atgctaagaa ggtaacatga | 2010 |

<210> SEQ ID NO 5
<211> LENGTH: 120
<212> TYPE: DNA
<213> ORGANISM: Artificial
<220> FEATURE:
<223> OTHER INFORMATION: primer

<400> SEQUENCE: 5

| | |
|---|---|
| atgagtaatc ctcaaaaagc tctaaacgac tgagccatat tcaacgggaa acgtcttgct | 60 |
| cagtttcatt tgatgctcga tgagtttttc cattatggta atgctaagaa ggtaacatga | 120 |

<210> SEQ ID NO 6
<211> LENGTH: 120
<212> TYPE: DNA
<213> ORGANISM: Artificial
<220> FEATURE:
<223> OTHER INFORMATION: primer

<400> SEQUENCE: 6

| | |
|---|---|
| gtcaaagtaa actacgagct actcaaaaag gtaataccat tactattctt ccattgtact | 60 |
| tcatgttacc ttcttatcat taccataatg gaaaaactca tcgagcatca atgaaactg | 120 |

<210> SEQ ID NO 7
<211> LENGTH: 100
<212> TYPE: DNA
<213> ORGANISM: Artificial
<220> FEATURE:
<223> OTHER INFORMATION: primer

<400> SEQUENCE: 7

| | |
|---|---|
| atgcttgctg tcagaagatt aacaagatac acattcctta gtgttgacaa ttaatcatcg | 60 |
| gcatagtata gggadgctcg aaggctttaa tttgcaagct | 100 |

<210> SEQ ID NO 8
<211> LENGTH: 150
<212> TYPE: DNA
<213> ORGANISM: Artificial
<220> FEATURE:
<223> OTHER INFORMATION: primer

<400> SEQUENCE: 8

| | |
|---|---|
| attgaagagc tagacatcga tgacgaatag cccctgcgag cttccgaaat taaacgttcg | 60 |

```
ataacttctc gatctgtagc tactgcttat tattcgtcat cgatgtctag ctcttcaata    120
gcttgcaaat taaagccttc gagcgtcccc                                    150
```

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9

```
ggatccatgc ctgctacttt acatgattct                                     30
```

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10

```
gtcgacatac ttgaatactt cgaaaggag                                      29
```

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11

```
actagtatgt ccgctaaatc gtttgaagtc                                     30
```

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12

```
atcgatatac aaggcgcttt gaaccccctt                                     30
```

<210> SEQ ID NO 13
<211> LENGTH: 27
<212> TYPE: DNA
<213> ORGANISM: Artificial
<220> FEATURE:
<223> OTHER INFORMATION: primer

<400> SEQUENCE: 13

```
gaattcatgt cgctgatcag catcctg                                        27
```

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14

```
actagtccag cattttaggt aaattccgtg                                     30
```

<210> SEQ ID NO 15
<211> LENGTH: 33

```
<212> TYPE: DNA
<213> ORGANISM: Artificial
<220> FEATURE:
<223> OTHER INFORMATION: primer

<400> SEQUENCE: 15
ggatccatgt cagcatttta ggtaaattcc gtg                              33

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16
ggatccataa tgtcgctgat cagcatcctg tct                              33

<210> SEQ ID NO 17
<211> LENGTH: 563
<212> TYPE: PRT
<213> ORGANISM: Saccharomyces cerevisiae

<400> SEQUENCE: 17
```

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
        290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
        370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
        450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 18
<211> LENGTH: 1689
<212> TYPE: DNA
<213> ORGANISM: Saccharomyces cerevisiae

<400> SEQUENCE: 18

```
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg tttttccacag aatgtctgcc aacatttctg aaaccactgc tatgatcact     420
```

```
gacattgcta ccgccccagc tgaaattgac agatgtatca gaaccactta cgtcacccaa    480
agaccagtct acttaggttt gccagctaac ttggtcgact tgaacgtccc agctaagttg    540
ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat gggtaactt cttgcaagaa    1140 ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta    1320 ttcattggtg acggttcttt gcaattgact gttcaagaaa tctccaccat gatcagatgg   1380
ggcttgaagc atacttgtt cgtcttgaac aacgatggt acaccattga aaagttgatt    1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaa                                                          1689
```

<210> SEQ ID NO 19
<211> LENGTH: 348
<212> TYPE: PRT
<213> ORGANISM: Saccharomyces cerevisiae

<400> SEQUENCE: 19

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140
```

```
Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
            165                 170                 175

Ser Gly Ala Ala Gly Leu Gly Ser Leu Ala Val Gln Tyr Ala Lys
        180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
        210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 20
<211> LENGTH: 1044
<212> TYPE: DNA
<213> ORGANISM: Saccharomyces cerevisiae

<400> SEQUENCE: 20
atgtctatcc agaaactcaa aaaggtgtt atcttctacg aatcccacgg taagttggaa      60
tacaaagata ttccagttcc aaagccaaag gccaacgaat gttgatcaa cgttaaatac    120 tctggtgtct gtcacactga cttgcacgct tggcacggtg actggccatt gccagttaag    180
ctaccattag tcggtggtca cgaaggtgcc ggtgtcgttg tcggcatggg tgaaaacgtt    240
aagggctgga agatcggtga ctacgccggt atcaaatggt tgaacggttc ttgtatggcc    300
tgtgaatact gtgaattggg taacgaatcc aactgtcctc acgctgactt gtctggttac    360
acccacgacg gttctttcca acaatacgct accgctgacg ctgttcaagc cgctcacatt    420
cctcaaggta ccgacttggc ccaagtcgcc cccatcttgt gtgctggtat caccgtctac    480
aaggctttga gtctgctaa cttgatggcc ggtcactggg ttgctatctc cggtgctgct    540
ggtggtctag ttcttttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttctac agatacgtt    780 agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
gacaccagag aagctttgga cttcttcgcc agaggtttgg tcaagtctcc aatcaaggtt    960
```

```
gtcggcttgt ctaccttgcc agaaatttac gaaaagatgg aaaagggtca aatcgttggt    1020
agatacgttg ttgacacttc taaa                                           1044
```

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21

```
ctgcagatga gttatactgt cggtacctat                                       30
```

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22

```
ttcggacaat tgttcgagga gatccgtacg                                       30
```

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23

```
tctagaatgg cttcttcaac tttttatatt                                       30
```

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24

```
cttgagaagg actcgcgaaa gattcagctg                                       30
```

<210> SEQ ID NO 25
<211> LENGTH: 337
<212> TYPE: PRT
<213> ORGANISM: Saccharomyces cerevisiae

<400> SEQUENCE: 25

```
Met Met Asp Lys His Lys Tyr Arg Val Glu Ile Gln Gln Met Met Phe
1               5                   10                  15

Val Ser Gly Glu Ile Asn Asp Pro Pro Val Glu Thr Thr Ser Leu Ile
            20                  25                  30

Glu Asp Ile Val Arg Gly Gln Val Ile Glu Ile Leu Leu Gln Ser Asn
        35                  40                  45

Lys Thr Ala His Leu Arg Gly Ser Arg Ser Ile Leu Pro Glu Asp Val
    50                  55                  60

Ile Phe Leu Ile Arg His Asp Lys Ala Lys Val Asn Arg Leu Arg Thr
65                  70                  75                  80

Tyr Leu Ser Trp Lys Asp Leu Arg Lys Asn Ala Lys Asp Gln Asp Ala
                85                  90                  95

Ser Ala Gly Val Ala Ser Gly Thr Gly Asn Pro Gly Ala Gly Gly Glu
```

```
            100                 105                 110
Asp Asp Leu Lys Lys Ala Gly Gly Glu Lys Asp Glu Lys Asp Gly
        115                 120                 125
Gly Asn Met Met Lys Val Lys Lys Ser Gln Ile Lys Leu Pro Trp Glu
    130                 135                 140
Leu Gln Phe Met Phe Asn Glu His Pro Leu Glu Asn Asn Asp Asp Asn
145                 150                 155                 160
Asp Asp Met Asp Glu Asp Glu Arg Glu Ala Asn Ile Val Thr Leu Lys
                165                 170                 175
Arg Leu Lys Met Ala Asp Asp Arg Thr Arg Asn Met Thr Lys Glu Glu
            180                 185                 190
Tyr Val His Trp Ser Asp Cys Arg Gln Ala Ser Phe Thr Phe Arg Lys
        195                 200                 205
Asn Lys Arg Phe Lys Asp Trp Ser Gly Ile Ser Gln Leu Thr Glu Gly
    210                 215                 220
Lys Pro His Asp Asp Val Ile Asp Ile Leu Gly Phe Leu Thr Phe Glu
225                 230                 235                 240
Ile Val Cys Ser Leu Thr Glu Thr Ala Leu Lys Ile Lys Gln Arg Glu
                245                 250                 255
Gln Val Leu Gln Thr Gln Lys Asp Lys Ser Gln Gln Ser Ser Gln Asp
            260                 265                 270
Asn Thr Asn Phe Glu Phe Ala Ser Ser Thr Leu His Arg Lys Lys Arg
        275                 280                 285
Leu Phe Asp Gly Pro Glu Asn Val Ile Asn Pro Leu Lys Pro Arg His
    290                 295                 300
Ile Glu Glu Ala Trp Arg Val Leu Gln Thr Ile Asp Met Arg His Arg
305                 310                 315                 320
Ala Leu Thr Asn Phe Lys Gly Gly Arg Leu Ser Ser Lys Pro Ile Ile
                325                 330                 335
Met

<210> SEQ ID NO 26
<211> LENGTH: 1011
<212> TYPE: DNA
<213> ORGANISM: Saccharomyces cerevisiae

<400> SEQUENCE: 26
atgatggaca agcataagta tcgtgtggag attcaacaga tgatgtttgt ctctggtgaa      60
attaacgacc cacccgtaga aaccacatca ctgatagaag atatagtgag gggtcaagtg     120
atagaaattc ttttacagtc aaacaaaacg gcgcatctta ggggaagtag gagcattctc     180
cctgaagacg tcattttctt gatcagacac gacaaggcca agtcaatcg tttgagaaca      240 tatctgtcat ggaaggattt gcgtaaaaac gccaaggacc aagatgctag tgccggtgta     300
gcgagtggca ctggaaatcc tggggcaggt ggtgaagatg atttgaaaaa agcaggtggt     360
ggcgagaaag acgaaaaaga tggtggaaac atgatgaagg tcaagaaatc ccaaattaag     420
ctgccatggg aattgcagtt tatgttcaat gaacatcctt tagaaaataa tgacgacaat     480
gatgatatgg atgaggatga acgagaagct aatatagtca ctttgaaaag gctgaaaatg     540
gctgacgata gaacacgaaa catgactaaa gaggagtacg tgcattggtc cgattgtcga     600
```

```
caggcaagtt ttacatttag gaagaataaa aggttcaagg actggtctgg aatttcgcaa      660
ttaactgagg ggaaacccca tgatgatgtg attgatatac tggggtttct aacttttgag      720
attgtctgtt ctttgacgga acagctctg aaaatcaaac aaagagaaca ggtattacag       780
actcaaaagg acaaatccca gcaatctagc caagataata ctaactttga atttgcatca      840
tccacattac atagaaagaa aagattattt gatggacctg aaaatgttat aaacccgctc      900
aaaccaaggc atatagagga agcctggaga gtactacaaa caattgacat gaggcatagg      960
gctttgacca actttaaagg tggtagactc agttctaaac caattatcat g              1011
```

<210> SEQ ID NO 27
<211> LENGTH: 240
<212> TYPE: PRT
<213> ORGANISM: Saccharomyces cerevisiae

<400> SEQUENCE: 27

```
Met Ala Asp Glu Glu Arg Leu Lys Glu Phe Lys Glu Ala Asn Lys Ile
1               5                   10                  15

Val Phe Asp Pro Asn Thr Arg Gln Val Trp Glu Asn Gln Asn Arg Asp
            20                  25                  30

Gly Thr Lys Pro Ala Thr Thr Phe Gln Ser Glu Glu Asp Ile Lys Arg
        35                  40                  45

Ala Ala Pro Glu Ser Glu Lys Asp Thr Ser Ala Thr Ser Gly Ile Val
    50                  55                  60

Pro Thr Leu Gln Asn Ile Val Ala Thr Val Thr Leu Gly Cys Arg Leu
65                  70                  75                  80

Asp Leu Lys Thr Val Ala Leu His Ala Arg Asn Ala Glu Tyr Asn Pro
                85                  90                  95

Lys Arg Phe Ala Ala Val Ile Met Arg Ile Arg Glu Pro Lys Thr Thr
            100                 105                 110

Ala Leu Ile Phe Ala Ser Gly Lys Met Val Val Thr Gly Ala Lys Ser
        115                 120                 125

Glu Asp Asp Ser Lys Leu Ala Ser Arg Lys Tyr Ala Arg Ile Ile Gln
    130                 135                 140

Lys Ile Gly Phe Ala Ala Lys Phe Thr Asp Phe Lys Ile Gln Asn Ile
145                 150                 155                 160

Val Gly Ser Cys Asp Val Lys Phe Pro Ile Arg Leu Glu Gly Leu Ala
                165                 170                 175

Phe Ser His Gly Thr Phe Ser Ser Tyr Glu Pro Glu Leu Phe Pro Gly
            180                 185                 190

Leu Ile Tyr Arg Met Val Lys Pro Lys Ile Val Leu Leu Ile Phe Val
        195                 200                 205

Ser Gly Lys Ile Val Leu Thr Gly Ala Lys Arg Glu Glu Ile Tyr
    210                 215                 220

Gln Ala Phe Glu Ala Ile Tyr Pro Val Leu Ser Glu Phe Arg Lys Met
225                 230                 235                 240
```

<210> SEQ ID NO 28
<211> LENGTH: 720
<212> TYPE: DNA
<213> ORGANISM: Saccharomyces cerevisiae

<400> SEQUENCE: 28

```
atggccgatg aggaacgttt aaaggagttt aaagaggcaa acaagatagt gtttgatcca       60
aataccagac aagtatggga aaaccagaat cgagatggta caaaaccagc aactactttc      120
```

```
cagagtgaag aggacataaa aagagctgcc ccagaatctg aaaaagacac ctccgccaca    180
tcaggtattg ttccaacact acaaaacatt gtggcaactg tgactttggg gtgcaggtta    240
gatctgaaaa cagttgcgct acatgcccgt aatgcagaat ataaccccaa gcgttttgct    300
gctgtcatca tgcgtattag agagccaaaa actacagctt taattttgc ctcagggaaa    360 atggttgtta ccgtgcaaa aagtgaggat gactcaaagc tggccagtag aaaatatgca    420
agaattatcc aaaaaatcgg gtttgctgct aaattcacag acttcaaaat acaaatatt    480 gtcggttcgt gtgacgttaa attccctata cgtctagaag ggttagcatt cagtcatggt    540
actttctcct cctatgagcc agaattgttt cctggtttga tctatagaat ggtgaagccg    600
aaaattgtgt tgttaattt tgtttcagga aagattgttc ttactggtgc aaagcaaagg    660
gaagaaattt accaagcttt tgaagctata taccctgtgc taagtgaatt tagaaaaatg    720
```

<210> SEQ ID NO 29
<211> LENGTH: 44
<212> TYPE: DNA
<213> ORGANISM: Artificial
<220> FEATURE:
<223> OTHER INFORMATION: primer

<400> SEQUENCE: 29

```
actagtcccg ccgccaccaa ggagatgatg gacaagcata agta                     44
```

<210> SEQ ID NO 30
<211> LENGTH: 26
<212> TYPE: DNA
<213> ORGANISM: Artificial
<220> FEATURE:
<223> OTHER INFORMATION: primer

<400> SEQUENCE: 30

```
actagtttac atgataattg gtttag                                         26
```

<210> SEQ ID NO 31
<211> LENGTH: 44
<212> TYPE: DNA
<213> ORGANISM: Artificial
<220> FEATURE:
<223> OTHER INFORMATION: primer

<400> SEQUENCE: 31

```
agatctcccg ccgccaccaa ggagatggcc gatgaggaac gttt                     44
```

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32

```
agatcttcac attttttctaa attcactta                                     29
```

TRANSFORMANT FOR ENHANCING BIOETHANOL PRODUCTION, AND METHOD FOR PRODUCING ETHANOL BY USING SAID STRAIN

CROSS-REFERENCE TO RELATED APPLICATIONS

This application is a U.S. national phase application under the provisions of 35 U.S.C. §371 of International Patent Application No. PCT/KR11/02712 filed Apr. 15, 2011, which in turn claims priority of Republic of Korea Patent Application No. 10-2010-0035853 filed Apr. 19, 2010, Republic of Korea Patent Application No. 10-2011-0003479 filed Jan. 13, 2011 and Republic of Korea Patent Application No. 10-2011-0003476 filed Jan. 13, 2011. The disclosures of such international patent application and Republic of Korea priority patent applications are hereby incorporated herein by reference in their respective entireties, for all purposes.

TECHNICAL FIELD

The present invention relates to a transformant for enhancing bioethanol production, which is prepared by deleting glycerol production genes from a *Saccharomyces cerevisiae* strain engineered so as to use glycerol as a fermentation source or by introducing the TATA-binding proteins SPT3 and STP15 into the *Saccharomyces cerevisiae* strain so as to overexpress the SPT3 and STP15 proteins, and to a method of producing ethanol using the transformant.

BACKGROUND ART

Ethanol currently has a huge market as an industrial solvent, and it is expected that ethanol can be actually used as a transportation fuel for automobiles and the like and the demand therefor continue to increase.

Glycerol ($C_3H_8O_3$) is converted from glucose ($C_6H_{12}O_6$) by one-step reduction and can provide improved reducing power during the metabolism of a microorganism. Many substances produced by fermentation frequently require reducing power in their metabolic pathways. Therefore, if glycerol can be effectively used as a substrate, the yield and productivity of the desired fermentation product can be improved. With a rapid increase in the production of biodiesel, the production of glycerol has increased, thus the price thereof is decreasing rapidly. As the production of biodiesel increases rapidly, the production of the byproduct glycerol also increases, and thus problems associated with the effective treatment of byproducts including glycerol will occur. Accordingly, the production of useful fermentation products by effective fermentation of glycerol will result in many effects.

The present inventors previously reported a transformant having an enhanced ability to produce ethanol from glycerol in *Saccharomyces cerevisiae* (Yu et al. Bioresour Technol. 101(11):4157-61 (2010)). In the studies of the present inventors, in order to increase ethanol productivity by improving a strain developed so as to use glycerol efficiently, an increase in glycerol productivity was achieved by blocking a pathway in which about 10% glycerol is produced as a byproduct in the production of ethanol in *Saccharomyces cerevisiae*.

Strains known to be used in the microbial production of glycerol include yeasts such as *S. cerevisiae, C. magnoliae, P. farinose, C. glycerinogens*, bacteria such as *B. subtilis*, and algae such as *D. tertiolecta*. It is known that microorganisms generated by manipulating the glycerol biosynthesis pathway found in microorganisms known as glycerol-producing strains can be used. Generally, a carbon substrate such as glucose is converted to glucose-6-phosphate by hexokinase in the presence of ATP. Glucose-6-phosphate is converted by glucose-phosphate isomerase to fructose-6-phosphate which is then converted to fructose-1,6-diphosphate by 6-phosphofructokinase. The fructose-1,6-diphosphate is converted to dihydroxyacetone phosphate (DHAP) by aldolase. Finally, DHAP is converted to glycerol-3-phosphate (G3P) by NADH-dependent glycerol-3-phosphate dehydrogenase (G3PDH), and the G3P is then dephosphorylated to glycerol by glycerol-3-phosphate phosphatase (Hou J et al. Appl Microbiol Biotechnol. 85(4):1123-30 (2010)).

Among dehydrogenase genes that are involved in DHAP conversion to glycerol, GPD1 is known as a gene encoding glycerol-3-phosphate dehydrogenase that converts DHAP to glycerol-3-phosphate. In addition, GPP2 from *Saccharomyces cerevisiae* is known as a gene encoding glycerol-3-phosphate phosphatase that converts glycerol-3-phosphate to glycerol.

In the glycerol production pathway in *Saccharomyces cerevisiae*, dihydroxyacetone phosphate (DHAP) is converted by glycerol-3-phosphate dehydrogenase (GPD) to glycerol-3-phosphate, which is then converted by glycerol-3-phosphate phosphatase to glycerol which is then excreted from cells through the glycerol export channel Fps1 (Oliveira et al. Biochim Biophys Acta. 27; 1613(1-2):57-71 (2003)).

In order to increase ethanol production in a transformant constructed so as to use glycerol as a carbon source in *Saccharomyces cerevisiae*, two glycerol production genes, glycerol-3-phosphate dehydrogenase 2 and yeast glycerol channel Fps1, were deleted. In addition, it was found that glycerol uptake protein (Gup1) provides recovery against osmotic stress, and an increase in ethanol production was achieved.

Further, the present inventors developed broad regulatory functions of sigma factors for facilitating whole cell manipulation by TATA-binding proteins overexpression and induction of multiple simultaneous gene expression changes similarly.

Particularly in the case of ethanol production, the present invention can be applied to fungal cells and RNA polymerase II factors related to such eukaryotic cells. The present invention may encompass the use of other eukaryotic cells and transcriptional mechanisms corresponding to such cells, for improving phenotype characteristics, particularly the resistance of glycerol (and other sugars) and/or ethanol in culture medium and the production of ethanol by cells from various sources known in the art.

Thus, in the present invention, in order to increase ethanol production in a *Saccharomyces cerevisiae* engineered so as to use glycerol as a carbon source, a transformant that overexpresses TATA-binding proteins SPT3 and SPT15 was constructed, thereby increasing ethanol production.

DISCLOSURE OF INVENTION

The present invention has been made in order to solve the above-described problems and to satisfy the above need, and an object of the present invention is to provide a strain improved to have an increased capability to produce bioethanol, the strain being obtained by blocking the glycerol production pathway in a yeast strain that produces bioethanol using glycerol as a fermentation source.

Another object of the present invention is to provide an improved yeast strain that can produce an increased amount of bioethanol using glycerol as a fermentation source.

Still another object of the present invention is to provide a method for preparing said transformant.

Yet another object of the present invention is to provide a method of producing ethanol using said transformant.

A further object of the present invention is to provide a composition for producing ethanol comprising said transformant.

To achieve the above objects, the present invention provides a transformant deleted for a glycerol-3-phosphate dehydrogenase 2 gene and an FPS1 (glycerol facilitator channel) gene encoding yeast glycerol channel FPS1.

In one embodiment of the present invention, the glycerol-3-phosphate dehydrogenase 2 preferably has an amino acid sequence set forth in SEQ ID NO: 1. However, a mutant comprising one or more mutations (such as substitution, deletion or addition) in the amino acid sequence of SEQ ID NO: 1 and having glycerol-3-phosphate dehydrogenase activity is also included in the definition of glycerol-3-phosphate dehydrogenase of the present invention.

In one embodiment of the present invention, the glycerol-3-phosphate dehydrogenase gene preferably has a nucleotide sequence set forth in SEQ ID NO: 2. However, in view of the degeneracy of the genetic code, a gene having a homology of at least 80%, preferably at least 85%, more preferably at least 90%, and most preferably at least 95%, with the nucleotide sequence of SEQ ID NO: 2, is also included in the definition of the glycerol-3-phosphate dehydrogenase gene of the present invention.

In another embodiment of the present invention, FPS1 encoding the yeast glycerol channel Fps1 preferably has an amino acid sequence set forth in SEQ ID NO: 3. However, a mutant comprising one or more mutations (such as substitution, deletion or addition) in the amino acid sequence of SEQ ID NO: 3) and having glycerol facilitator channel activity is also included in the definition of the yeast glycerol channel of the present invention.

In still another embodiment of the present invention, the FPS1 gene encoding the yeast glycerol channel Fps1 preferably has a nucleotide sequence set forth in SEQ ID NO: 4. However, in view of the degeneracy of the genetic code, a gene having a homology of at least 80%, preferably at least 85%, more preferably at least 90%, and most preferably at least 95%, with the nucleotide sequence of SEQ ID NO: 4, is also included in the definition of the yeast glycerol channel gene of the present invention.

In one embodiment of the present invention, the deleted genes, glycerol-3-phosphate dehydrogenase 2 and yeast glycerol channel FPS1, are preferably derived from yeasts, and more preferably Saccharomyces cerevisiae microorganisms, but are not limited thereto.

The transformant of the present invention is derived from yeasts, preferably Saccharomyces cerevisiae microorganisms, but is not limited thereto.

The present invention also provides a method for preparing a transformant deleted for a glycerol-3-phosphate dehydrogenase 2 gene and a FPS1 (glycerol facilitator channel) gene encoding yeast glycerol channel FPS1, the method comprising the steps of: a) performing PCR using pPICZ vector DNA having a cleavage map of FIG. 8 as a template, a forward primer comprising the sequence from start codon to 40-mer of yeast glycerol channel FPS1 and a reverse primer comprising the sequence from residue 1971 to stop codon of yeast glycerol channel FPS1, thereby obtaining a PCR product comprising the start and stop codons of Fps1 gene; b) performing PCR using pET28a vector DNA having a cleavage of FIG. 9 as a template, a forward primer comprising the sequence from start codon to 40-mer of glycerol-3-phosphate dehydrogenase 2 and a reverse primer comprising the sequence from residue 1324 to stop codon of glycerol-3-phosphate dehydrogenase 2, thereby obtaining a PCR product; and c) performing homologous recombination of the PCR products of steps a) and b) in yeast.

In one embodiment of the present invention, the forward primer comprising the sequence from start codon to 40-mer of yeast glycerol channel FPS1, and the reverse primer comprising the sequence from residue 1971 to stop codon of yeast glycerol channel FPS1 are preferably primers set forth in SEQ ID NO: 5 and SEQ ID NO: 6, respectively, but are not limited. In addition, the forward primer comprising the sequence from start codon to 40-mer of glycerol-3-phosphate dehydrogenase 2, and the reverse primer comprising the sequence from residue 1324 to stop codon of glycerol-3-phosphate dehydrogenase 2 are preferably primers set forth in SEQ ID NO: 7 and SEQ ID NO: 8, respectively, but are not limited thereto.

The present invention also provides a transformant comprising, in addition to the above-described transformant, glycerol dehydrogenase, dihydroxyacetone kinase, and glycerol uptake protein genes.

In one embodiment of the present invention, the transformant is preferably yeast Saccharomyces cerevisiae YPH499fps1$^\Delta$gpd2$^\Delta$ (pGcyaDak, pGup1Cas) (accession number: KCCM11071P), but is not limited thereto.

The present invention also provides an expression vector pGcyaDakAdhPdc comprising a gene encoding Saccharomyces cerevisiae pyruvate decarboxylase and a gene encoding alcohol dehydrogenase.

In one embodiment of the present invention, the pyruvate decarboxylase preferably has an amino acid sequence set forth in SEQ ID NO: 17. However, a mutant comprising one or more mutations (such as substitution, deletion or addition) in the amino acid sequence of SEQ ID NO: 17 and having glycerol-3-phosphate dehydrogenase activity is also included in the definition of the pyruvate decarboxylase of the present invention.

In one embodiment of the present invention, the gene encoding the pyruvate decarboxylase preferably has a nucleotide sequence in SEQ ID NO: 18. However, in view of the degeneracy of the genetic code, a gene having a homology of at least 80%, preferably at least 85%, more preferably at least 90%, and most preferably at least 95%, with the nucleotide sequence of SEQ ID NO: 18, is also included in the definition of the pyruvate decarboxylase of the present invention.

In another embodiment of the present invention, the alcohol dehydrogenase preferably has an amino acid sequence set forth in SEQ ID NO: 19. However, a mutant comprising one or more mutations (such as substitution, deletion or addition) in SEQ ID NO: 19 and having alcohol dehydrogenase activity is also included in the definition of the alcohol dehydrogenase of the present invention.

In still another embodiment of the present invention, the gene encoding alcohol dehydrogenase preferably has a nucleotide sequence set forth in SEQ ID NO: 20. However, in view of the degeneracy of the genetic code, a gene having a homology of at least 80%, preferably at least 85%, more preferably 90%, and most preferably at least 95%, is also included in the definition of the alcohol dehydrogenase of the present invention.

In one embodiment of the present invention, the expression vector is preferably the expression vector pGcyaDakAdhPdc having a cleavage map shown in FIG. 11, but is not limited thereto.

The present invention also provides a transformant comprising, in addition to the above-described transformant of the present invention, either a gene encoding *Saccharomyces cerevisiae* pyruvate decarboxylase and a gene encoding alcohol dehydrogenase, or an expression vector pGcyaDakAdhPdc containing a gene encoding *Saccharomyces cerevisiae* pyruvate decarboxylase and a gene encoding alcohol dehydrogenase.

In one embodiment of the present invention, the transformant is derived from yeasts, preferably *Saccharomyces cerevisiae* microorganisms, but is not limited thereto.

The present invention also provides a method for preparing a transformant for producing ethanol using glycerol, the method comprising steps a) to c) of the above preparation method and a step of transforming the transformant of step c) with recombinant vectors pGcyaDak and pGupCas.

In one embodiment of the present invention, the recombinant vectors pGcyaDak and pGupCas preferably have cleavage maps shown in FIGS. 4 and 5, respectively, but are not limited thereto.

The present invention also provides an expression vector pGupSpt3.15 containing *Saccharomyces cerevisiae* SPT (Suppressor of Ty)3 and SPT (Suppressor of Ty) 15 (hereinafter referred to as "SPT 3" and "SPT15", respectively) genes.

In one embodiment of the present invention, the TATA-binding protein SPT3 preferably has an amino acid sequence set forth in SEQ ID NO: 25. However, a mutant comprising one or more mutations (such as substitution, deletion or addition) in the amino acid sequence of SEQ ID NO: 25 and having SPT3 activity is also included in the definition of SPT3 of the present invention.

In another embodiment of the present invention, the TATA-binding protein SPT3 preferably has a nucleotide sequence set forth in SEQ ID NO: 26. However, in view of the degeneracy of the genetic code, a gene having a homology of at least 80%, preferably at least 85%, more preferably at least 90%, and most preferably at least 95%, with the nucleotide sequence of SEQ ID NO: 26, is also included in the definition of the SPT3 gene of the present invention.

In still another embodiment of the present invention, the TATA-binding protein SPT15 preferably has an amino acid sequence set forth in SEQ ID NO: 27. However, a mutant comprising one or more mutations (such as substitution, deletion or addition) in the amino acid sequence of SEQ ID NO: 27 and having TATA-binding protein SPT15 activity is also included in the definition of the TATA-binding protein SPT15 of the present invention.

In yet another embodiment of the present invention, the TATA-binding protein SPT15 preferably has a nucleotide sequence set forth in SEQ ID NO: 28. However, in view of the degeneracy of the genetic code, a gene having a homology of at least 80%, preferably at least 85%, more preferably at least 90%, and most preferably at least 95%, with the nucleotide sequence of SEQ ID NO: 28, is also included in the definition of the TATA-binding protein SPT15 of the present invention.

In one embodiment of the present invention, the expression vector of the present invention preferably has a cleavage map shown in FIG. 14, but is not limited thereto.

The present invention also provides a transformant prepared by introducing the expression vector pGupSpt3.15 of the present invention into the transformant containing the glycerol dehydrogenase, dihydroxyacetone kinase and glycerol uptake protein genes, wherein the transformant is preferably yeast *Saccharomyces cerevisiae* YPH499 (pGcyaDak, pGupSpt3.15Cas) (accession number: KCCM 11153P), but is not limited thereto.

The present invention also provides a method for producing ethanol, comprising a step of culturing the transformant of the present invention using glycerol as a substrate.

In one embodiment of the present invention, the glycerol is preferably glycerol produced as a byproduct of biodiesel production, but is not limited thereto.

The present invention also provides a composition for producing ethanol, comprising the transformant of the present invention. The inventive composition for producing ethanol comprises, for example, a polypeptide, a broth, a cell lysate, a purified or non-purified enzyme extract or a polypeptide, which is suitable for producing ethanol by culturing the transformant using glycerol as a substrate.

If yeast is used as a host, examples of an expression vector that may be used in the present invention include YEp13, YCp50, pRS and pYEX vectors. Examples of a promoter that may be used in the present invention include a GAL promoter, an AOD promoter and the like. Examples of a method that may be used for introduction of recombinant DNA into yeast include an electroporation method (Method Enzymol., 194, 182-187 (1990)), a spheroplast method (Proc. Natl. Acad. Sci. USA, 84, 1929-1933 (1978)), a lithium acetate method (J. Bacteriol., 153, 163-168 (1983)) and the like.

Also, the recombinant vector may have fragment for inhibition of expression which has a variety of functions for suppression, amplification or triggering of expression, a marker for selection of a transformant; a antibiotic resistance gene, or a gene encoding a signal for extracellular secretion.

The transformant of the present invention may be cultured by a conventional method which used for culture of hosts.

The culture of the transformant may be carried out using any conventional method for microbial culture, including a batch culture method, a fed-batch culture method, a continuous culture method, and a reactor-type culture method. Examples of a medium for culturing the transformant using bacteria such as *E. coli* a host include complete media or synthetic, for example, LB medium, NB medium and the like. Also, the transformant is cultured at a predetermined temperature, so that glycerol dehydrogenase and dihydroxyacetone kinase or glycerol uptake protein are accumulated in microbial and collected.

Carbon sources are required for the proliferation of microorganisms, and examples thereof include sugars such as glucose, fructose, sucrose, maltose, galactose or starch; lower alcohols such as ethanol, propanol or butanol; polyhydric alcohols such as glycerol; organic acids such as acetic acid, citric acid, succinic acid, tartaric acid, lactic acid or gluconic acid; and fatty acids such as propionic acid, butanoic acid, pentanoic acid, hexanoic acid, heptanoic acid, octanoic acid, nonanoic acid, decanoic acid, undecanoic acid or dodecanoic acid.

Examples of nitrogen sources include ammonium salts, such as ammonia, ammonium chloride, ammonium sulfate or ammonium phosphate, and materials of natural origin, such as peptone, meat juice, yeast extracts, malt extracts, casein hydrolysates, or corn steep liquor. In addition, examples of minerals include monopotassium phosphate, dipotassium phosphate, magnesium phosphate, magnesium sulfate, sodium chloride and the like. The medium may be supplemented with an antibiotic such as kanamycin, ampicillin, tetracycline, chloramphenicol or streptomycin.

Also, when microorganisms transformed with an expression vector having an inducible promoter are cultured, an inducer suitable for the kind of promoter may be added to the medium. Examples of the inducer include isopropyl-$\beta$-D-thiogalactopyranoside (IPTG), tetracycline, indole acrylic acid (IAA), and the like.

Glycerol dehydrogenase and dihydroxyacetone kinase or glycerol uptake protein can be obtained by centrifuging the culture medium of the transformant, collecting a cell or a supernatant from the centrifuged medium, and subjecting the collected cell or supernatant to one or a combination of two or more selected from cell lysis, extraction, affinity chromatography, cation or anion exchange chromatography, and gel filtration.

The determination of whether the resulting purified substance is the desired yeast can be performed using a conventional method, for example, SDS-polyacrylamide gel electrophoresis or Western blotting.

Hereinafter, the present invention will be described.

The present invention relates to a transformant having an increased ability to produce the main product bioethanol, the transformant being prepared by deleting glycerol production genes from a *Saccharomyces cerevisiae* (manipulated so as to use glycerol as a fermentation source) so as to reduce the production of the byproduct glycerol, and a method for producing ethanol using the transformant. More specifically, the present invention relates to a yeast transformant having an increased ability to produce ethanol while having a reduced ability to produce glycerol, the yeast transformant being prepared by deleting two glycerol production genes, glycerol-3-phosphate dehydrogenase 2 and FPS1 encoding yeast glycerol channel Fps1p from *Saccharomyces cerevisiae*, and a method for producing an increased amount of ethanol using the transformant.

In the present invention, it was found that, when glycerol-3-phosphate dehydrogenase 2 and FPS1 encoding yeast glycerol channel Fps1p from *Saccharomyces cerevisiae* are deleted from a *Saccharomyces cerevisiae*, the ability of the resulting strain to produce glycerol is decreased while the ability to produce ethanol is increased, and when the strain having the increased ability to produce ethanol is transformed with genes that efficiently use glycerol, the transformed strain has an increased ability to produce ethanol, compared to existing transformants. Also, in the present invention, the glycerol uptake protein from *Saccharomyces cerevisiae* microorganisms is an enzyme allowing glycerol permeation and helping to have resistance to osmotic pressure when glycerol is used as a fermentation source in a strain having a reduced ability to produce glycerol.

In addition, the inventive yeast transformant having a reduced ability to produce glycerol, prepared from *Saccharomyces cerevisiae* microorganisms constructed so as to use glycerol as a carbon source, can be effectively used in processes. The results of fermentation carried out using glycerol as a substrate indicated that the yeast transformant deleted for the above genes produced a larger amount of ethanol compared to a transformant from which the above genes have not been deleted.

Hereinafter, the present invention will be described in detail.

In the glycerol production pathway in *Saccharomyces cerevisiae*, dihydroxyacetone phosphate (DHAP) is converted by glycerol-3-phosphate dehydrogenase (GPD) to glycerol-3-phosphate, which is then converted by glycerol-3-phosphate phosphatase to glycerol which is then excreted from cells through the glycerol export channel Fps1. In the present invention, glycerol-3-phosphate dehydrogenase and yeast glycerol channel Fps1 gene are deleted from the strain engineered so as to use glycerol as a carbon source, thereby increasing ethanol production in the strain.

In one example of the present invention, PCR was performed using pPICZ vector DNA as a template, a forward primer comprising the sequence from start codon to 40-mer of Fps1 and a reverse primer comprising the stop codon of Fps1, thereby obtaining a 1.5-kb PCR product. The obtained Zeocin-resistant gene PCR product was subjected to homologous recombination, thereby constructing a Fps1 gene-deleted strain. Also, PCR was performed using pET28a vector DNA as a template, a forward primer comprising the sequence from start codon to 40-mer of Gpd2 and a reverse primer comprising the stop codon of Gpd2, thereby obtaining a 1.5-kb PCR product, and the obtained kanamycin-resistant gene PCR product was subjected to homologous recombination in yeast, thereby constructing a strain deleted for Fps1 and Gpd2 gene. Then, yeast host cells were transformed with the recombinant vector having Gcy and Dak inserted therein. Then, for insertion of Gup1 gene, a yeast-integration vector was constructed and inserted into *Saccharomyces cerevisiae*. The production of ethanol in the resulting strain using glycerol was examined.

As a result, it could be seen that ethanol production in the recombinant transformant YPH499fps1$^\Delta$gpd2$^\Delta$ (pGcyaDak, pGup1Cas) according to the present invention was increased.

Accordingly, in order to increase ethanol production in yeast *Saccharomyces cerevisiae* that uses glycerol as a fermentation source, the present inventors developed a yeast transformant by deleting glycerol-3-phosphate dehydrogenase (gpd2) and yeast glycerol channel Fps1 genes from *Saccharomyces cerevisiae*, transforming the strain with a recombinant vector containing genes which allow the strain to use glycerol, and introducing glycerol uptake protein (Gup1) into the strain. The developed strain was deposited with the Korean Culture Center of Microorganisms (KCCM) (Yurim Building, Hongje-1-dong, Seodaemun-Ku, Seoul, Korea) on Mar. 10, 2010 under the accession number KCCM11071P. In addition, it was found that the yeast transformant efficiently produces an increased amount of ethanol by efficiently using glycerol as a carbon source, thereby completing the present invention.

Further, it was found that ethanol production is further increased by the overexpression of pyruvate decarboxylase and alcohol dehydrogenase in the *Saccharomyces cerevisiae* strain having an increased ability to produce ethanol as a result of the deletion of glycerol-3-phosphate dehydrogenase (gpd) and glycerol channel Fps1 genes which are involved in glycerol production in *Saccharomyces cerevisiae*.

In one example of the present invention, 1.6-kb PDC1 and 1.0-kb ADH1 fragments were obtained by performing PCR using *Saccharomyces cerevisiae* as a template. The obtained PCR products were cloned into pGcyaDak gene, which was then transformed into the yeast strain in which the glycerol production pathway has been impaired, thereby constructing a strain having a higher ability to produce ethanol. For insertion of Gup1 gene, a yeast-integration vector was constructed and inserted into the *Saccharomyces cerevisiae* strain. Ethanol production in this strain using glycerol was examined.

As a result, it could be seen that ethanol production in the recombinant transformant *Saccharomyces cerevisiae* YPH499fps1$^\Delta$gpd2$^\Delta$ (pGcyaDak, pGupCas) was increased.

Accordingly, in order to increase the production of ethanol in yeast *Saccharomyces cerevisiae*, a typical strain which produces ethanol using glycerol, the present inventors developed a yeast *Saccharomyces cerevisiae* transformant which overexpresses pyruvate decarboxylase and alcohol dehydrogenase and in which the glycerol production pathway was blocked. The developed yeast transformant was named "*Saccharomyces cerevisiae* YPH499fps1$^\Delta$gpd2$^\Delta$ (pGcyaDakAdhPdc, pGupCas)" and deposited with the Korean Culture Center of Microorganisms (KCCM) (Yurim Building, Hong-1-donor, Seodaemun-Ku, Seoul, Korea) on Dec. 17, 2010 under the accession number KCCM11152P. In addition, it was found that the yeast transformant efficiently produces an increased amount of ethanol by efficiently using glycerol as a carbon source.

In the present invention, in order to increase ethanol production in the *Saccharomyces cerevisiae* transformant constructed so as to use glycerol as a carbon source, a gene encoding *Saccharomyces cerevisiae* pyruvate decarboxylase and a gene encoding alcohol dehydrogenase were introduced into the transformant strain deleted for two glycerol production genes, glycerol-3-phosphate dehydrogenase 2 and yeast glycerol channel Fps1, and it was found that ethanol production in this strain was increased.

The present invention is also directed to a *Saccharomyces cerevisiae* transformant which has an increased ability to produce bioethanol, the transformant being prepared by introducing the TATA-binding proteins SPT3 and SPT15 into the *Saccharomyces cerevisiae* strain engineered so as to use glycerol as a fermentation source, so that the TATA-binding proteins SPT3 and SPT3 are overexpressed in the transformant, and to a method for producing ethanol using the transformant. More particularly, the present invention is directed to a *Saccharomyces cerevisiae* transformant having an increased ability to produce ethanol and having increased resistance to osmotic stress, the transformant being prepared by introducing yeast RNA polymerase factors, for example, SPT3 and SPT15, into the *Saccharomyces cerevisiae* strain constructed so as to use glycerol as a fermentation source, so that SPT3 and SPT15 are overexpressed in the transformant, and to a method for producing an increased amount of ethanol using the transformant.

In the present invention, it was found that, when the *Saccharomyces cerevisiae* transformant strain, which overexpresses the TATA-binding proteins SPT3 and SPT15 to increase the ethanol production ability and resistance to osmotic stress, is transformed with a gene that efficiently uses glycerol, the resulting strain has an increased ability to produce ethanol, compared to existing transformants. In addition, the inventive yeast transformant having a reduced ability to produce glycerol, prepared from the *Saccharomyces cerevisiae* strain constructed so as to use glycerol as a carbon source, can be effectively used in processes. The results of fermentation carried out using glycerol as a substrate indicated that the yeast transformant deleted for the above genes produced a larger amount of ethanol compared to a transformant from which the above genes have not been deleted.

In one example of the present invention, 1.0-kb SPT3 and 0.7-kb SPT15 fragments were obtained by PCR using *Saccharomyces cerevisiae* as a template, and the obtained PCR products were transformed into yeast, thereby constructing a strain overexpressing the TATA-binding proteins SPT3 and SPT15. Then, yeast host cells were transformed with a recombinant vector containing Gcy and Dak inserted therein. Then, for insertion of Gup1 gene, a yeast-integration vector was constructed and inserted into *Saccharomyces cerevisiae*. The production of ethanol in the resulting strain using glycerol was examined.

As a result, it could be seen that ethanol production in the recombinant transformant YPH499 (pGcyaDak, pGupSpt3.15Cas) according to the present invention was increased.

This developed transformant was deposited with the Korean Culture Center of Microorganisms (KCCM) (Yurim Building Hongje-1-dong, Seodaemun-Ku, Seoul, Korea) on December 2010 under the accession number KCCM11153P.

ADVANTAGEOUS EFFECTS

As described above, in the present invention, glycerol production in a *Saccharomyces cerevisiae* strain was inhibited by deleting glycerol-3-phosphate dehydrogenase (gpd2) and yeast glycerol channel Fps1 (glycerol export channel) from the strain. In addition, a recombinant vector containing glycerol uptake protein was introduced into a yeast transformant introduced with glycerol dehydrogenase and dihydroxyacetone kinase genes. Then, it was found that ethanol production in the transformant was increased compared to that in the yeast strain. The inventive yeast transformant constructed by deleting glycerol production genes from the strain engineered so as to use glycerol as a carbon source can produce a large amount of ethanol using a glycerol which is produced as a byproduct of biodiesel production, and thus the present invention is a very useful invention.

The overexpression of pyruvate decarboxylase and alcohol dehydrogenase genes in the strain led to an increase in ethanol production. It was found that, when these pyruvate decarboxylase and alcohol dehydrogenase genes were introduced into the yeast strain obtained by inserting glycerol uptake protein into the transformant from which the gpd2 and Fps1 genes have been deleted to inhibit glycerol production and into which glycerol dehydrogenase and dihydroxyacetone kinase genes have been introduced, the resulting transformant strain has an increased ability to produce ethanol, compared to a yeast strain which does not contain the transformant containing pyruvate decarboxylase and alcohol dehydrogenase.

In addition, it was found that ethanol production in the transformant, which overexpresses the TATA-binding proteins SPT3 and SPT15 to increase ethanol production, was increased compared to that in a strain which does not overexpress the binding proteins.

BRIEF DESCRIPTION OF THE DRAWINGS

FIG. 6(A) shows a medium containing glycerol as a carbon source, and FIG. 6(B) shows a YPD medium containing 1 M NaCl and 10 mM glycerol. Lane 1: YPH499 (pESC-TRP); lane 2: YPH499fps1Δgpd2 (pESC-TRP); lane 3: YPH499fps1Δgpd2 (pGcyaDak); and lane 4: YPH499fps1Δgpd2Δ (pGcyaDak,pGupCas).

In FIG. 7, ■: YPH499 (pGcyaDak,pGupCas); and ♦: YPH499fps1Δgpd2Δ (pGcyaDak,pGupCas).

In FIG. 5, black ▲: YPH499 (pESC-TRP); green: ♦: *Saccharomyces cerevisiae* YPH499fps1$^\Delta$gpd2$^\Delta$ (pGcyaDak, pGupCas); red ■: *Saccharomyces cerevisiae* YPH499fps1$^\Delta$gpd2$^\Delta$ (pGcyaDakAdhPdc, pGupCas).

In FIG. 16, ♦: YPH499 (pESC-TRP); ■: YPH499 (pGcyaDak, pGupCas); and ▲: YPH499 (pGcyaDak, pGupSpt3Cas); X, YPH499 (pGcyaDak, pGupSpt3.15Cas).

BEST MODE FOR CARRYING OUT THE INVENTION

Examples

Hereinafter, the present invention will be described in further detail with reference to examples. It will be obvious to a person having ordinary skill in the art that these examples are illustrative purposes only and are not to be construed to limit the scope of the present invention.

Example 1

Deletion of Yeast Glycerol-3-Phosphate Dehydrogenase (gpd2) and Yeast Glycerol Channel Fps1

In order to impair the glycerol production pathway by deleting glycerol-3-phosphate dehydrogenase (gpd2) and yeast glycerol channel Fps1 genes, PCR was performed using the DNA of a pPICZ vector (Invitrogen, USA; FIG. 7a) as a template, a forward primer comprising the sequence from start codon to 40-mer of Fps1 (5-atgagtaatcct-caaaaagctctaaacgactgagccatattcaacgggaaacgtcttgctc agtttcatttgatgctcgatgagttttccattatggtaatgctaagaaggtaacatga-3; SEQ ID NO: 5) and a reverse primer comprising the sequence the stop codon of Fps1 (5'-gtcaaagtaaactacgagctact-caaaaaggtaataccattactattcttccattgtactt catgttaccttcttatcattac-cataatggaaaaactcatcgagcatcaaatgaaactg-3'; SEQ ID NO: 6), thereby obtaining a 1.5-kb PCR product flanked by the start codon and stop codon of Fps1 and having zeocin resistance.

Figure 1:
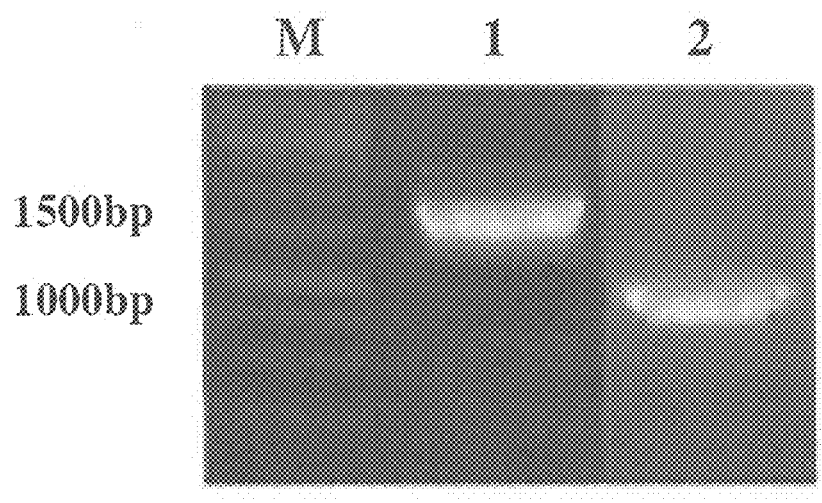
FIG. 1 shows the results of agarose gel electrophoresis of the homology arms of a PCR product, conducted to confirm homology arms for the deletion of glycerol-3-phosphate dehydrogenase 2 and FPS1 genes. Lane 1 shows 1-kb DNA marker; Lane 2 shows that a Fps1 homology arm was formed at the 5' and 3' ends of a zeocin resistance gene to delete Fps1 gene; and Lane 3 shows that a Gpd2 homology arm was formed at the 5' and 3' ends of a kanamycin resistance gene to delete Gpd2 gene.
Figure 2:
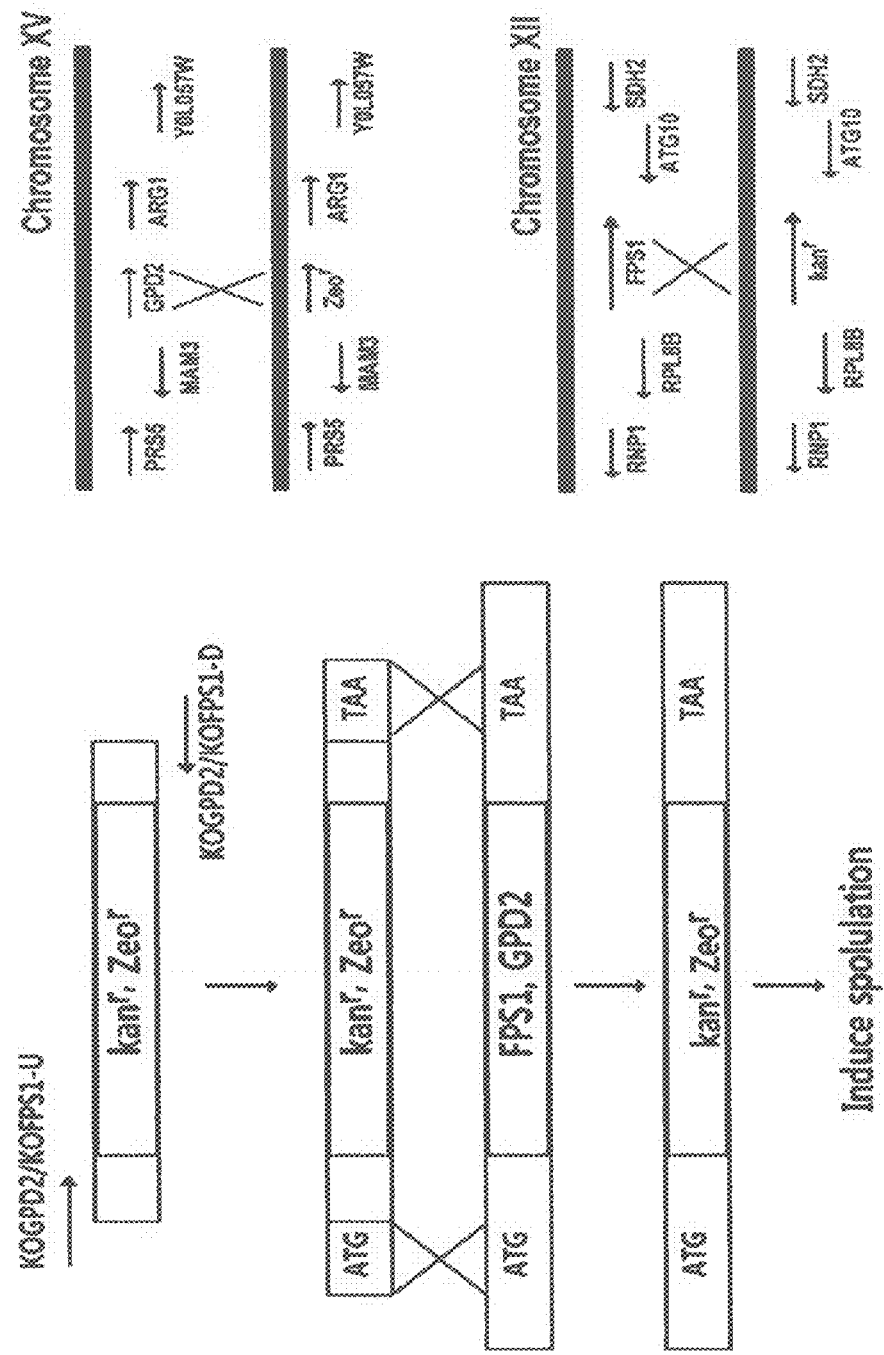
FIG. 2 is a schematic diagram showing a method of deleting glycerol-3-phosphate dehydrogenase 2 and FPS1 genes according to the present invention.

For deletion of Gpd2 gene, in the same manner, PCR was performed using the DNA of a pET28a vector (Invitrogen, USA; FIG. 7b) as a template, a forward primer (5-atgcttgct-gtcagaagattaacaagatacacattccttagtgttgacaattaatcatcgg catag-tatagggadgctcgaaggctttaatttgcaagct-3; SEQ ID NO: 7) and a reverse primer (5'-attgaagagctagacatcgatgacgaat-agcccctgcgagcttccgaaattaaacgttcga taacttctcgatctgtagctact-gcttattattcgtcatcgatgtctagctcttcaatagc ttgcaaattaaagccttc-gagcgtcccc; SEQ ID NO: 8), thereby obtaining a 1.5-kb PCR product having kanamycin resistance. The obtained PCR products were subjected to homologous recombination in yeast YPH499 (MATa ura3-52lys2-801_amberade2-101_ochretrp1-Δ63his3-Δ2001eu2-Δ1) (Clontech Laboratories, Inc.), thereby constructing a strain deleted for the Fps1 and Gpd2 genes. Then, the gene deletion strain was selected using an YPD medium (1% yeast extract, 2% Bacto peptone, and 2% glucose, 2% agar) containing zeocin and kanamycin. FIG. 1 shows the results of agarose gel electrophoresis of the PCR products, and FIG. 2 shows a method of deleting the gpd2 and Fps1 genes as described above. The obtained strain was named "*Saccharomyces cerevisiae* YPH499fps1$^\Delta$gpd2$^\Delta$".

Example 2

Transformation with Glycerol Dehydrogenase, Dihydroxyacetone Kinase and Glycerol Uptake Protein Genes Example 2-1

Figure 3:
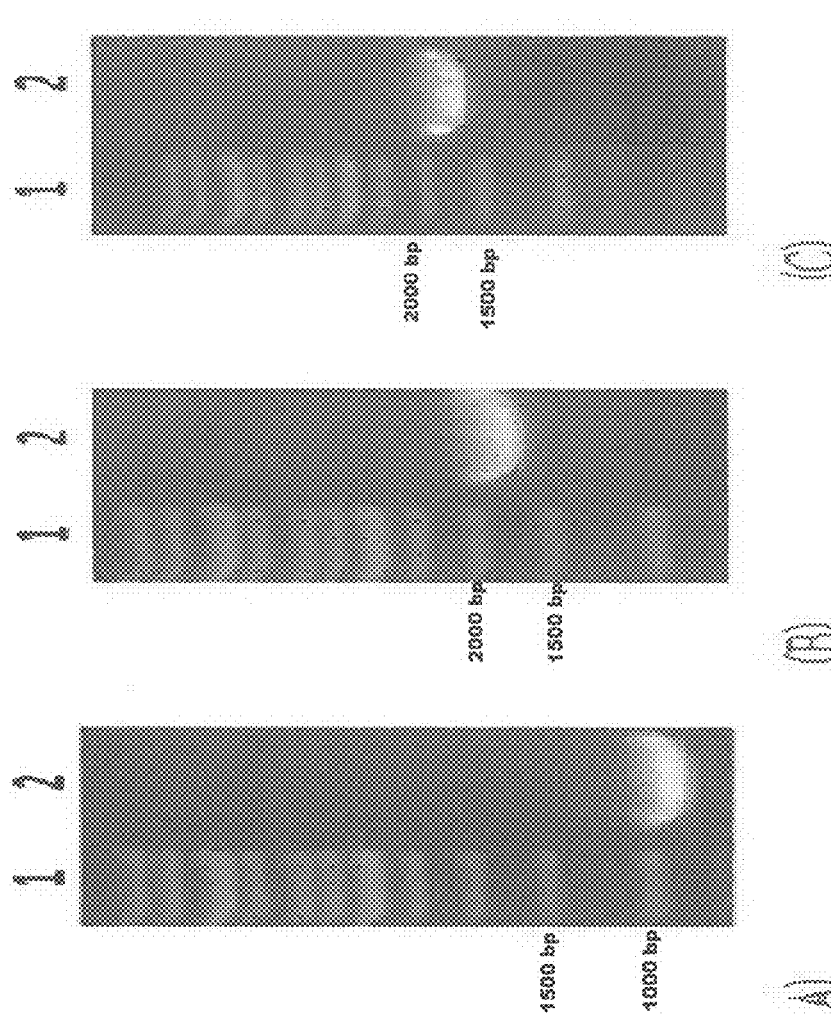
FIG. 3(A) shows the results of agarose gel electrophoresis of the PCR product of a glycerol dehydrogenase gene in the present invention. Lane 1: 1-kb DNA marker; and lane 2: Gcy PCR product.
FIG. 3(B) shows the results of agarose gel electrophoresis of the PCR product of a dihydroxyacetone kinase gene in the present invention. Lane 1: 1-kb DNA marker; and lane 2: Dak PCR product.
FIG. 3(C) shows the results of agarose gel electrophoresis of the PCR product of a glycerol uptake protein gene in the present invention. Lane 1: 1-kb DNA marker; and lane 2: Gup PCR product.

Amplification of Yeast Glycerol Dehydrogenase, Dihydroxyacetone Kinase and Glycerol Uptake Protein Genes In order to clone glycerol dehydrogenase and dihydroxyacetone kinase genes for efficiently converting glycerol to the intermediate DHAP, the following primers containing recognition sequences were designed and synthesized with reference to the nucleotide sequences of peptide moieties from *Saccharomyces cerevisiae* genomic DNA (BY4741): for cloning of Gcy, BamH (5-ggatccatgcctgctactttacatgattct-3; SEQ ID NO: 9), and Sal (5-gtcgacatacttgaatacttcgaaaggag-3; SEQ ID NO: 10); for Dak, Spe (5-actagtatgtccgctaaatcgtttgaagtc-3; SEQ ID NO: 11), and Cla (5-atcgatata-caaggcgctttgaaccccctt-3; SEQ ID NO: 12); and for Gup1, EcoR (5-gaattcatgtcgctgatcagcatcctg-3; SEQ ID NO: 13), and Sp e(5-actagtccagcattttaggtaaattccgtg-3; SEQ ID NO: 14). Then, PCR was performed using the synthesized primers. As a result, as shown in FIG. 3, 936-bp, 1755-bp and 1683-bp PCR bands could be confirmed.

Example 2-2

Cloning of Glycerol Dehydrogenase, Dihydroxyacetone Kinase and Glycerol Uptake Protein Genes The amplification products obtained in Example 2-1 were electrophoresed on 0.8% agarose gel, and the DNA fragments on the agarose gel were recovered using a Biospin gel extraction kit (Bioflux).

Figure 4:
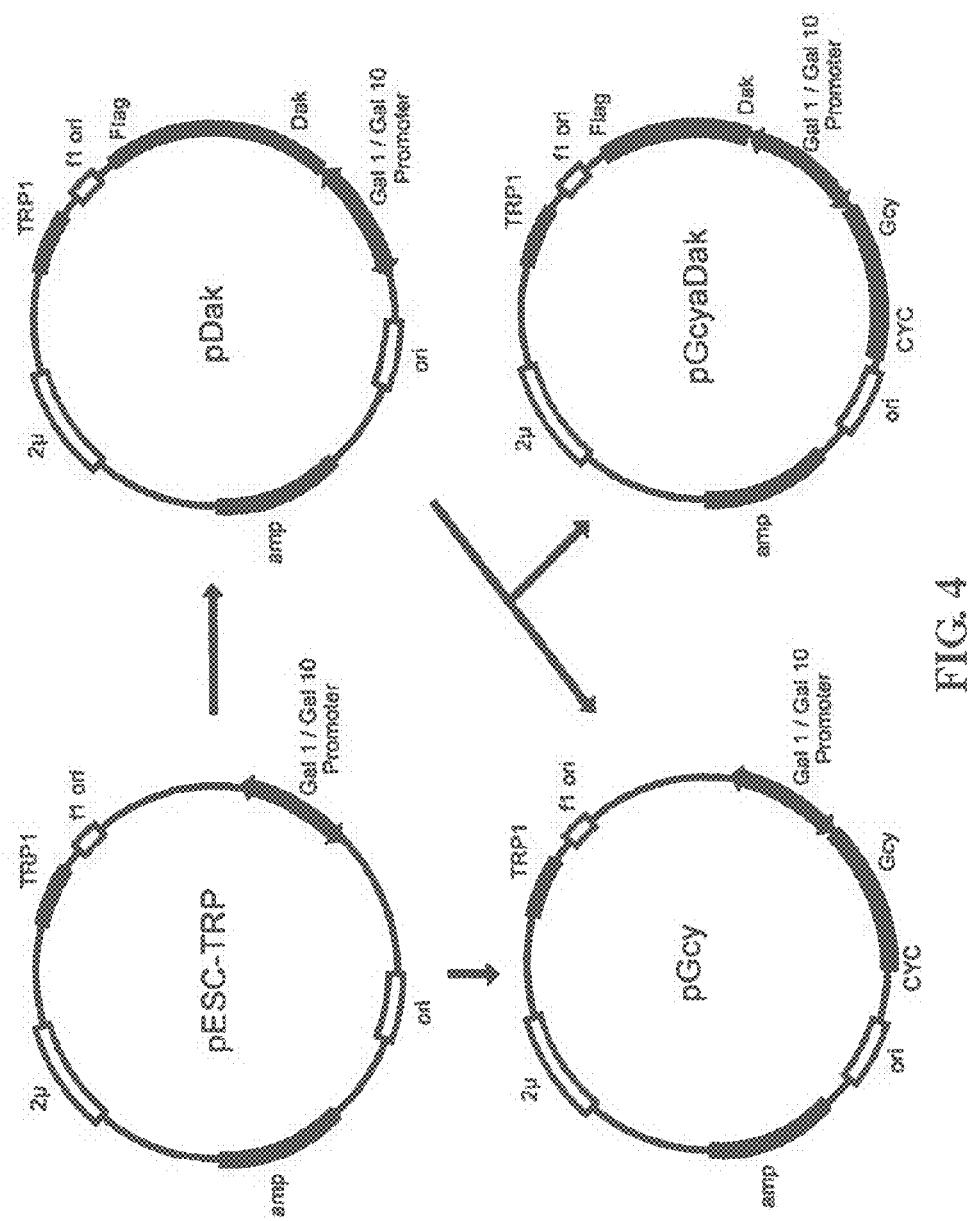
FIG. 4 is a schematic diagram showing a process of preparing the recombinant vector pGcyaDak containing the glycerol dehydrogenase and dihydroxyacetone kinase genes inserted therein according to the present invention.
Figure 5:
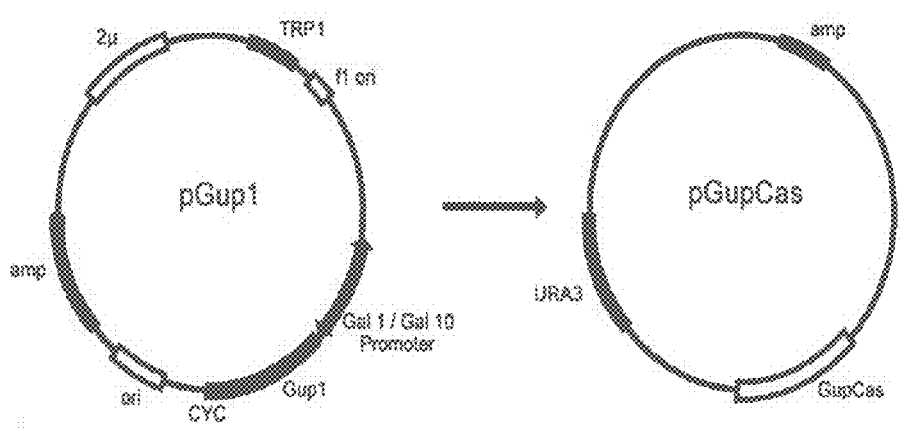
FIG. 5 is a schematic diagram showing a process of preparing the recombinant vector pGup for insertion of glycerol uptake protein according to the present invention.

Then, Gcy was digested with BamH and Sal, Dak was digested with Spe and Cla, and Gup1 was digested with EcoR and Spe, and each of the digested genes was ligated into a pESC-trp (Clontech) (yeast-E. coli shuttle vector) which was then transformed into E. coli DH5a. Then, ligated recombinant plasmid DNAs were separated from the transformed cells. The recombinant vectors were named "pESC-Gcy", "pESC-Dak", and "pESC-Gup", respectively. Then, Dak was cloned into the pESC-Gcy vector which was then transformed into E. coli DH5a (Invitrogen). Then, the ligated recombinant plasmid DNA was separated from the transformant. This recombinant vector was named "pGcyaDak" and is shown in FIG. 4. Meanwhile, in order to insert pESC-Gup1, a sense primer (5-ggatccatgt cagcattttaggtaaattccgtg-3; SEQ ID NO: 15) and an anti-sense primer (5-ggatccataatgtcgctgatcagcatc-ctg tct-3; SEQ ID NO: 16) were constructed so as to contain a BamH1 recognition sequence, and using these primers, pESC-Gup1 was cloned into the yeast integration vector YIP-5 which was then inserted into Saccharomyces cerevisiae genomic DNA.

The recombinant vector pGcyaDak, pGupCas was transformed into the gene deletion strain (YPH499fps1$^\Delta$gpd2$^\Delta$) using a YEASTMAKER yeast transformation kit2 (Clontech) according to the manufacturer's instruction. Then, the transformant was selected using a tryptophan-deficient SD medium (0.67% yeast nitrogen base, 2% glucose, 0.067% yeast nitrogen base w/o trp, 2% agar) containing zeocin and kanamycin and was named "Saccharomyces cerevisiae YPH499fps1$^\Delta$gpd2$^\Delta$ (pGcyaDak, pGupCas).

Example 3

Transformation with Genes Encoding Yeast Pyruvate Decarboxylase and Alcohol Dehydrogenase Example 3-1

Amplification of Yeast PDC1 and ADH1

Figure 10:
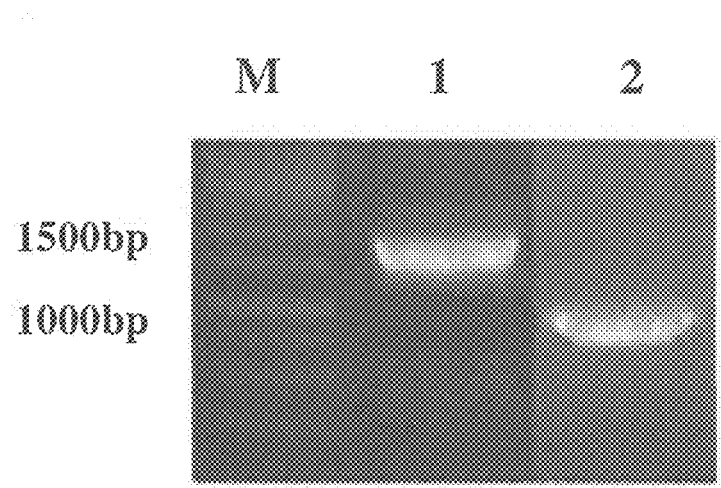
FIG. 10 shows the results of agarose gel electrophoresis conducted to confirm genes which encode pyruvate decarboxylase and alcohol dehydrogenase. Lane 1: 1-kb DNA marker; lane 2: PDC1 gene; lane 3: ADH1 gene.

In order to clone the two key enzymes PDC1 and ADH1 which are involved in conversion from pyruvate to ethanol and are overexpressed to increases ethanol production, the following primers containing recognition sequences were designed and synthesized with reference to the nucleotide sequences of peptide moieties from Saccharomyces cerevisiae genomic DNA (BY4741): for cloning of PDC, Pst (5-ct-gcagatga gttatactgt cggtacctat-3; SEQ ID NO: 21), and Sph (5-ttcggacaat tgttcgagga gatccgtacg-3; SEQ ID NO: 22); and for ADH, Xba (5-tctagaatgg cttcttcaac tttttatatt-3; SEQ ID NO: 23), and Sal (5-cttgagaagg actcgcgaaa gattcagctg-3; SEQ ID NO: 24). PCR was performed using the synthesized primers. As a result, as shown in FIG. 10, 1.6-kb and 1.0-kb PCR bands could be confirmed.

Example 3-2

Cloning of Yeast PDC1 and ADH1 Genes

The amplification products obtained in Example 3-1 were electrophoresed on 0.8% agarose gel, and the DNA fragments on the agarose gel were recovered using a Biospin gel extraction kit (Bioflux).

Then, PDC1 was digested with Pst and Sph, and ADH1 was digested with Xba and Sal, and then the genes were digested with the respective restriction enzymes.

Figure 11:
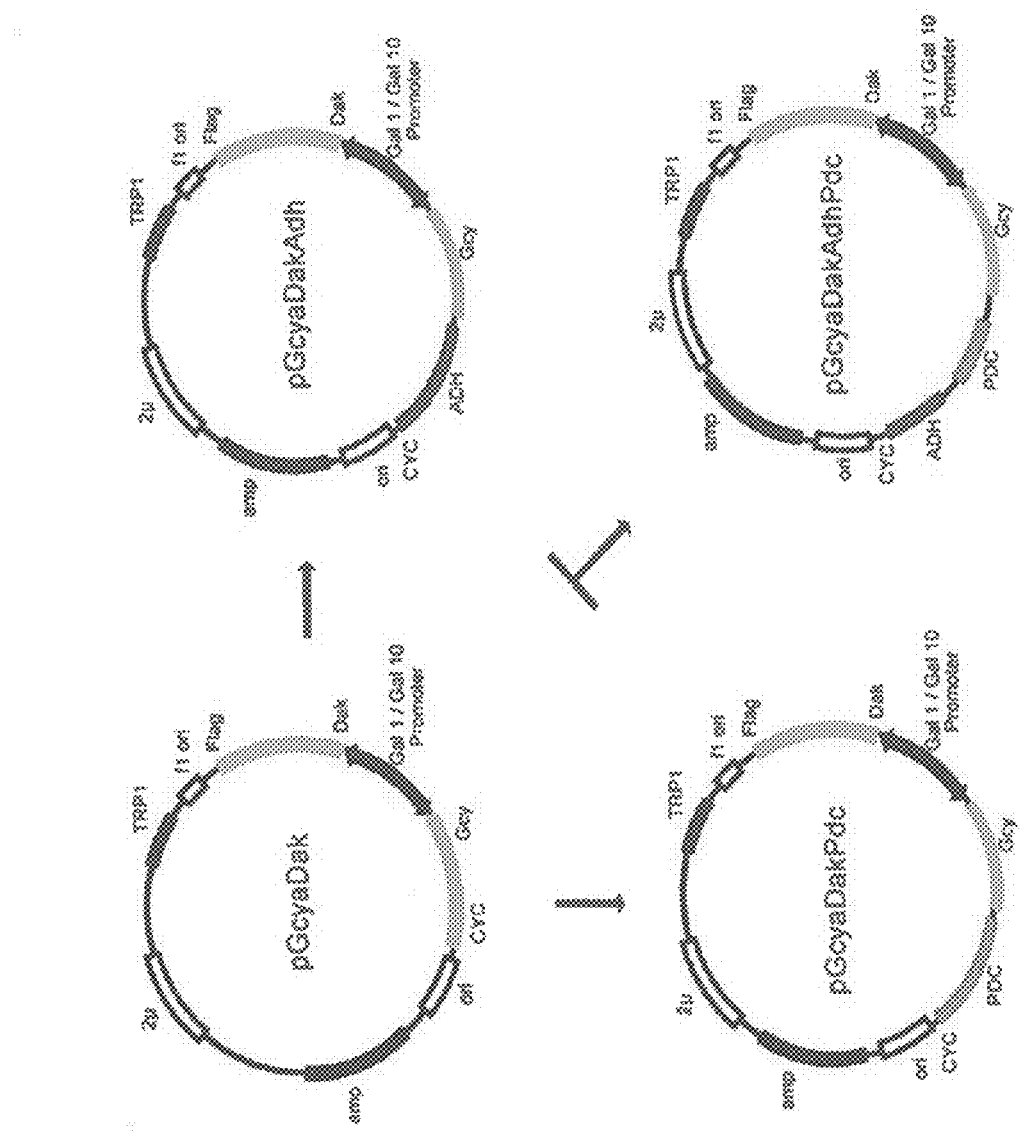
FIG. 11 is a schematic diagram showing a process of inserting pyruvate decarboxylase and alcohol dehydrogenase genes into the recombinant vector pGcyaDak in which glycerol dehydrogenase and dihydroxyacetone kinase genes have been inserted.

The digested genes were ligated into the vector pGcyaDak inserted with the glycerol dehydrogenase and dihydroxyacetone kinase genes, and then the vector was transformed into E. coli DH5a (Invitrogen). Then, ligated recombinant plasmid DNA was separated from the transformant. The recombinant vector was named "pGupCaspGcyaDakAdhPdc" and shown in FIG. 11.

The recombinant vector pGcyaDakAdhPdc, pGupCas was transformed into the mutant strain (YPH499fps1gpd2), in which the glycerol production pathway had been impaired, using a YEASTMAKER yeast transformation kit2 (Clontech) according to the manufacturer's instruction. Then, the transformant was selected using a tryptophan-deficient SD medium (0.67% yeast nitrogen base, 2% glucose, 0.067% yeast nitrogen base w/o trp, 2% agar) and was named "Saccharomyces cerevisiae YPH499fps1$^\Delta$gpd2$^\Delta$ (pGcyaDakAdh-Pdc, pGupCas)".

Example 4

Transformation with Yeast TATA-Binding Proteins SPT3 and SPT15

Example 4-1

Amplification of Yeast TATA-Binding Proteins SPT3 and SPT15

Figure 13:
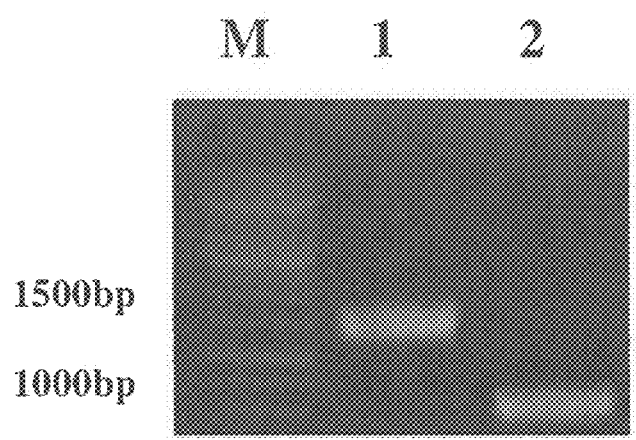
FIG. 13 shows the results of agarose gel electrophoresis conducted to confirm the presence of the TATA-binding proteins SPT3 and SPT15. Lane 1: 1-kb DNA marker; lane 2: SPT3; and lane 3: SPT15.

In order to clone the TATA-binding proteins SPT3 and SPT15 which increase ethanol production and resistance to osmotic stress in a process of producing ethanol using glycerol as a substrate, the following primers containing recognition sequences were designed and synthesized with reference to the nucleotide sequences of peptide moieties from Saccharomyces cerevisiae genomic DNA (BY4741): for cloning of SPT3, Spe (5-actagtcccg ccgccaccaa ggagatgatg gacaagcata agta-3; SEQ ID NO: 29), and Spe (5-actagtttac atgataattg gtttag-3; SEQ ID NO: 30); and for SPT15, Bgl (5-agatctcccg ccgccaccaa ggagatggcc gatgaggaac gttt-3; SEQ ID NO: 31), and Bgl (5-agatcttcac atttttctaa attcactta-3; SEQ ID NO: 32). Then, PCR was performed using the synthesized primers. As a result, as shown in FIG. 13, 1.5-kb and 0.7-kb PCR bands could be confirmed.

Example 4-2

Cloning of Yeast TATA-Binding Proteins SPT3 and SPT15

The amplification products obtained in Example 4-1 were electrophoresed on 0.8% agarose gel, and the DNA fragments on the agarose gel were recovered using a Biospin gel extraction kit (Bioflux).

Figure 14:
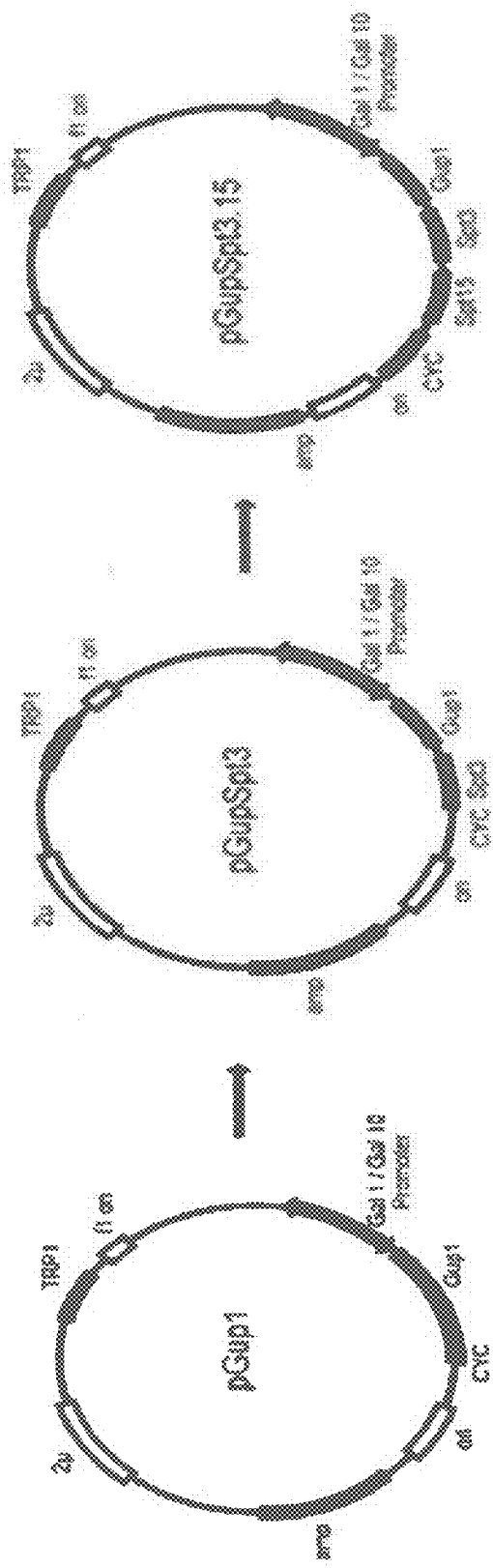
FIG. 14 is a schematic diagram showing a process of constructing the recombinant vector pGupSpt3.15Cas by inserting the TATA-binding proteins SPT3 and SPT15 into the recombinant vector pGup containing glycerol uptake protein gene.
Figure 15:
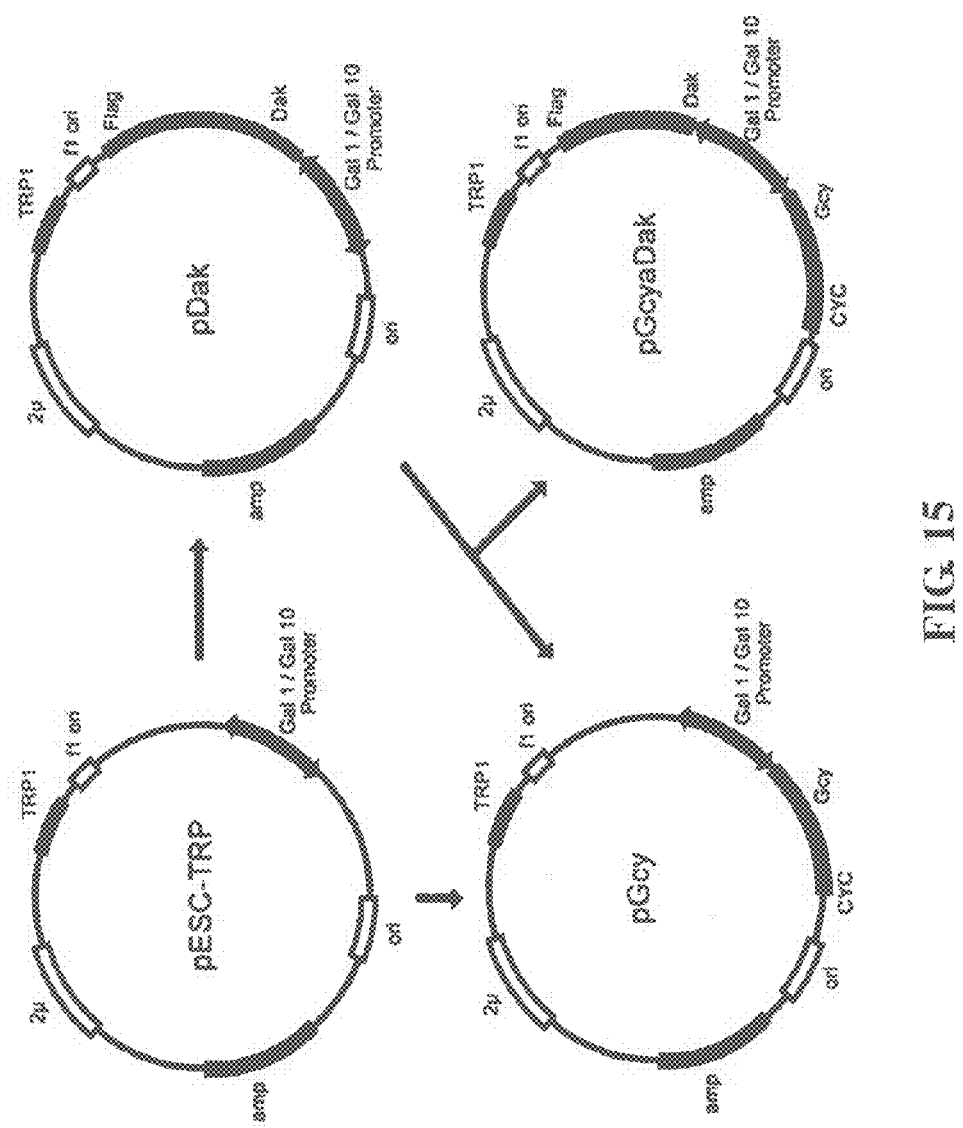
FIG. 15 is a schematic diagram showing a process of constructing the recombinant vector pGcyaDak containing the glycerol dehydrogenase and dihydroxyacetone kinase genes inserted therein according to the present invention.

Then, SPT3 was digested with Spe, and Dak was digested with Bgl, followed by digestion with the restriction enzymes Spe1 and Bgl, respectively. Then, the genes were ligated into the vector pGup1 inserted with glycerol uptake protein, and then the vector was transformed into *E. coli* DH5a (Invitrogen). Then, ligated recombinant plasmid DNA was separated from the transformant. The recombinant vector was named "pGupSpt3, pGupSpt3.15" and is shown in FIG. 14.

To insert the vector pGupSpt3.15, a sense primer (5-ggatccatgt cagcattttaggtaaattccgtg-3; SEQ ID NO: 15) and an antisense primer (5-ggatccataatgtcgctgatcagcatcctg tct-3; SEQ ID NO: 16) were constructed so as to contain a BamH1 recognition sequence, and using these primers, pGupSpt3.15 was cloned into the yeast integration vector YIP-5 (ATCC). The resulting construct was named "pGupSpt3.15Cas" and shown in FIG. 14. The pGupSpt3.15Cas was inserted into *Saccharomyces cerevisiae* genomic DNA. The recombinant vector pGupSpt3.15Cas was transformed into a wild type strain (YPH499, Clontech Laboratories Inc.) using a YEAST-MAKER yeast transformation kit2 (Clontech) according to the manufacturer's instruction. Then, the transformant was selected using tryptophan-deficient SD medium (0.67% yeast nitrogen base, 2% glucose, 0.067% yeast nitrogen base w/o trp, 2% agar) and was named "*Saccharomyces cerevisiae* YPH499 (pGcyaDak, pGupSpt3.Spt15Cas)".

Example 5

Figure 6:
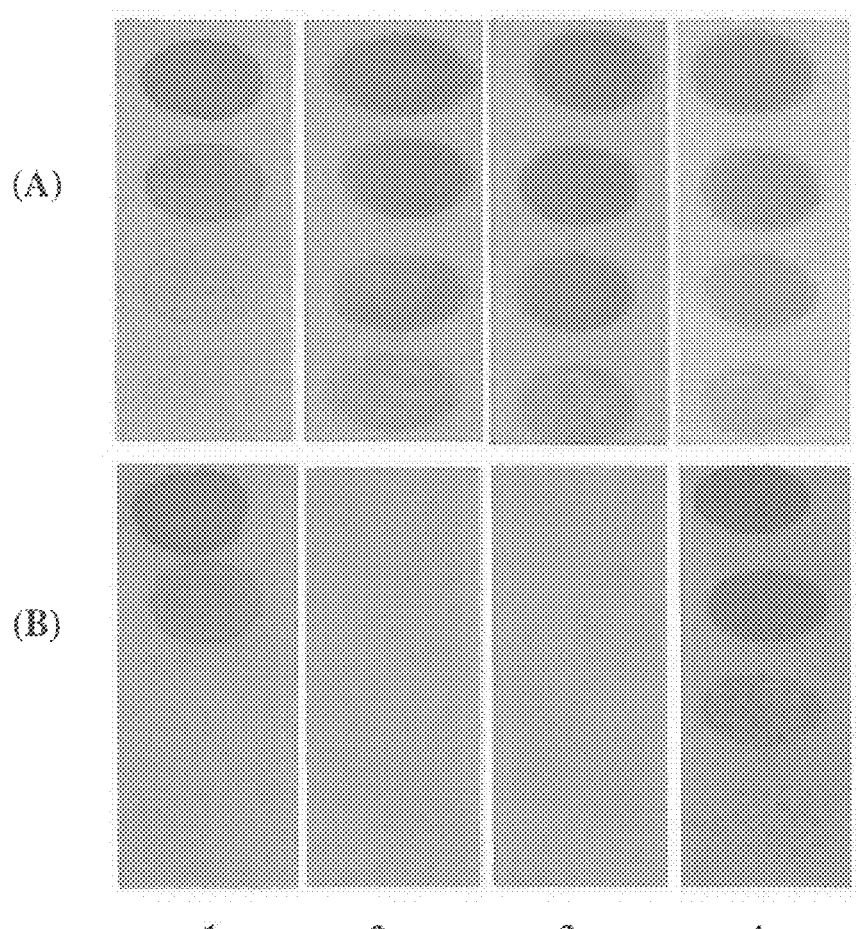
FIG. 6 shows the influence of osmotic stress on the gene deletion strain YPH499fps1$^\Delta$gpd2$^\Delta$ according to the present invention and shows that the strain recovers from osmotic stress by pGup1cas.

Measurement of Influence of Osmotic Stress on Strain in which Glycerol Production Pathway has been Impaired In order to measure the influence of osmotic stress on the strain from which the glycerol-3-phosphate dehydrogenase 2 and yeast glycerol channel Fps1 genes were deleted, a growth test was carried out in different media. Specifically, the strain was cultured in a medium containing glucose as a carbon source, and then diluted to an OD600 of 1, followed by dilution to 1/10. 10 μl of the dilution was dispensed while the formation of colonies was examined. To examine the influence of osmotic stress, NaCl was used at increasing concentrations. The results of the test are shown in FIG. 6.

Example 6

Production of Bioethanol Using Yeast Transformant

Figure 7:
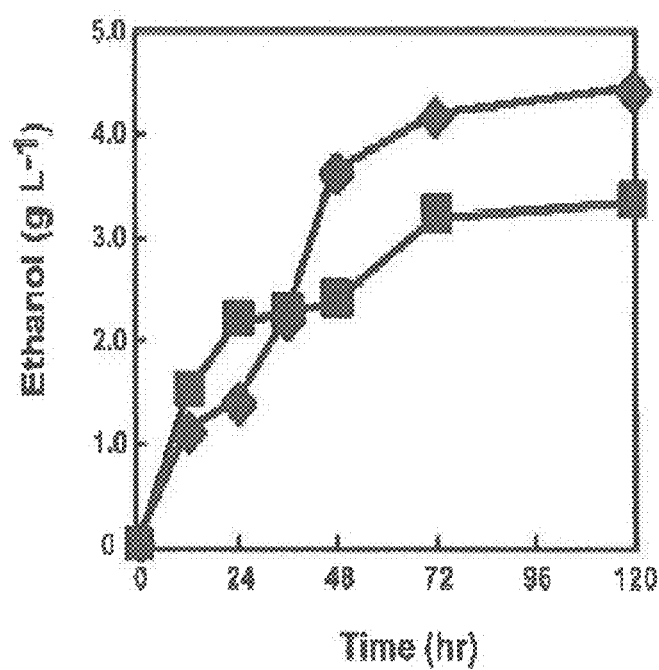
FIG. 7 is a graph showing that, when the gene deletion strain according to the present invention is transformed with the recombinant vector pGcyaDak, pGup, the ability of the strain to produce using ethanol as a substrate is increased.
Figure 8:
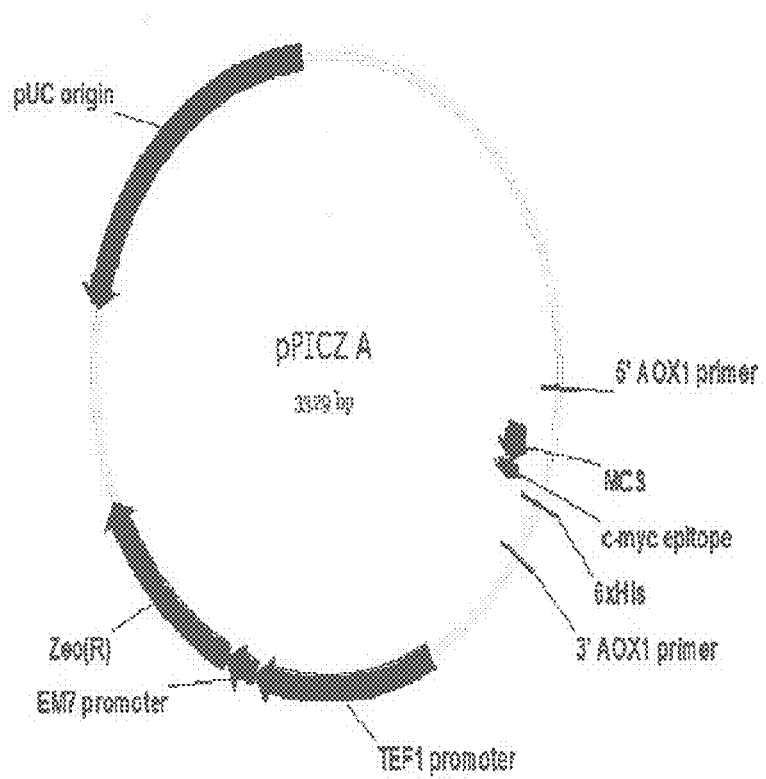
FIG. 8 is a cleavage map of a pPICZ vector.
Figure 9:
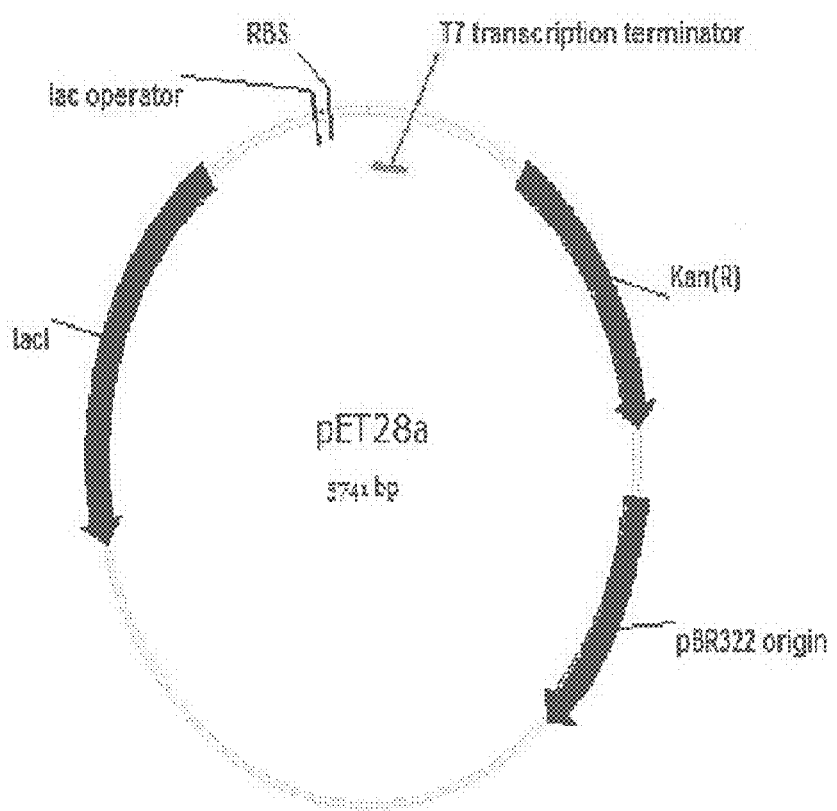
FIG. 9 is a cleavage map of a pET28a vector.

Each of YPH499fps1$^\Delta$gpd2 (pGcyaDak, pGupCas) prepared in Example 2 and YPH499 (pGcyaDak, pGupCas) was pre-cultured in an SG medium containing galactose for 24 hours, and then shake-cultured in a fermentation medium containing 2% glycerol as a substrate for 48 hours until the absorbance at 600 nm reached 1. Each of the fermentation cultures was incubated at 30° C. and 100 rpm while it was sampled at varying points of time and subjected to gas chromatography to measure the production of ethanol. As a result, it was shown that the production of ethanol in YPH499fps1$^\Delta$gpd2$^\Delta$ (pGcyaDak, pGupCas) deleted for glycerol-3-phosphate dehydrogenase 2 and yeast glycerol channel Fps1 genes was higher than that in YPH499 (pGcyaDak, pGupCas). The results of the measurement are shown in FIG. 7.

Example 7

Production of Bioethanol Using Yeast Transformant

Figure 12:
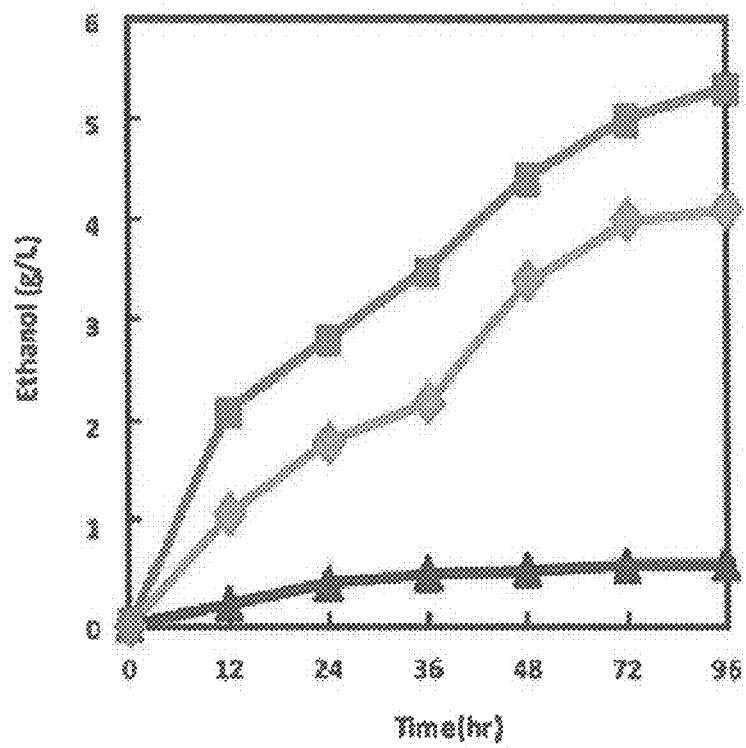
FIG. 12 is a graph showing that, when the gene deletion strain according to the present invention is transformed with the recombinant vector pGcyaDakAdhPdc, pGup, the ability of the strain to produce ethanol using glycerol as a substrate is increased.

Each of *Saccharomyces cerevisiae* YPH499fps1$^\Delta$gpd2$^\Delta$ (pGcyaDak, pGupCas) prepared in Example 2 and *Saccharomyces cerevisiae* YPH499fps1$^\Delta$gpd2$^\Delta$ (pGcyaDakAdhPdc, pGupCas) prepared in Example 3 was pre-cultured in an SG medium containing galactose for 24 hours, and then shake-cultured in a fermentation medium containing 2% glycerol as a substrate for 48 hours until the absorbance at 600 nm reached 1. Each of the fermentation cultures was incubated at 30° C. and 100 rpm while it was sampled at varying points of time and subjected to gas chromatography to measure the production of ethanol. As a result, it was found that the production of ethanol in *Saccharomyces cerevisiae* YPH499fps1$^\Delta$gpd2$^\Delta$ YPH499fps1gpd2 (pGcyaDakAdhPdc, pGupCas), in which pyruvate decarboxylase and alcohol dehydrogenase genes were overexpressed, was higher than that in *Saccharomyces cerevisiae* YPH499fps1$^\Delta$gpd2$^\Delta$ (pGcyaDak, pGupCas). The results of the measurement are shown in FIG. 12.

Example 8

Production of Bioethanol Using Yeast Transformant

Figure 16:
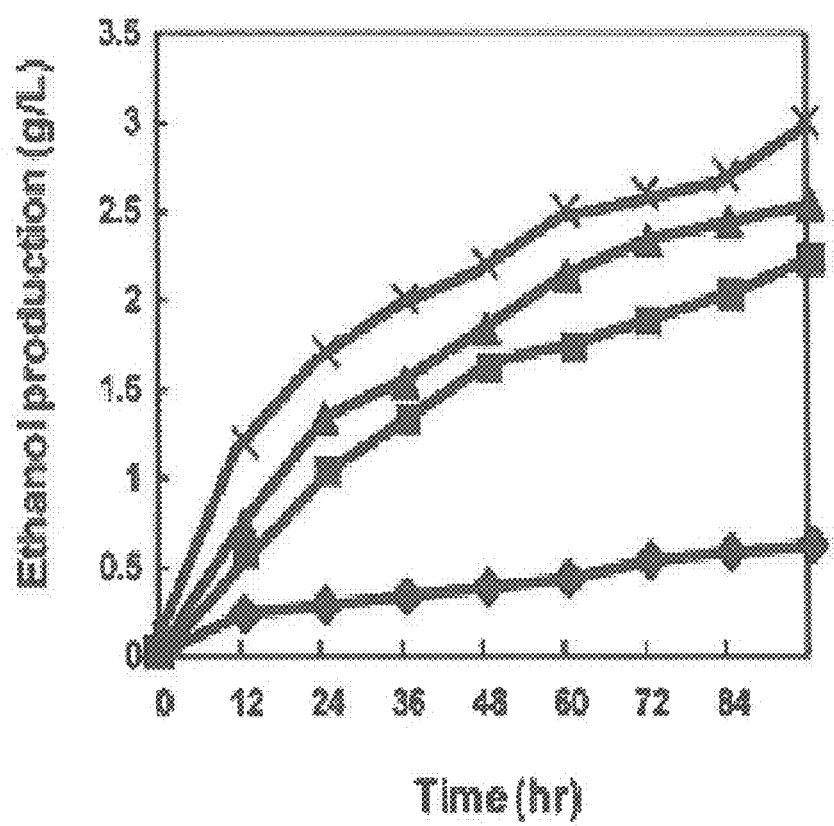
FIG. 16 is a graph showing that, when a vector overexpressing the TATA-binding proteins SPT3 and SPT15 according to the present invention is transformed with pGcyaDak, the ability of the vector to produce ethanol using glycerol as a substrate is increased.

Each of YPH499 (pGcyaDak, pGupCas) and the YPH499 (pGcyaDak, pGupSpt3.15Cas) prepared in Example 4 was pre-cultured in an SG medium containing galactose for 24 hours, and then shake-cultured in a fermentation medium containing 2% glycerol as a substrate for 48 hours until the absorbance at 600 nm reached 1. Each of the fermentation cultures was incubated at 30° C. and 100 rpm while it was sampled at varying points of time and subjected to gas chromatography to measure the production of ethanol. As a result, it was shown that the production of ethanol in the strain, in which the TATA-binding proteins were overexpressed, was higher than that in YPH499 (pGcyaDak, pGupCas). The results of the measurement are shown in FIG. 16.

The invention claimed is:

1. A genetically engineered yeast cell, wherein said cell comprises: a disruption of a gene encoding glycerol-3-phosphate dehydrogenase 2 and a disruption of a FPS1 (glycerol facilitator channel) gene encoding yeast glycerol channel FPS1, wherein said cell further comprises a gene encoding glycerol dehydrogenase, a gene encoding dihydroxyacetone kinase, and a gene encoding glycerol uptake protein, wherein said cell comprises a gene encoding *Saccharomyces cerevisiae* pyruvate decarboxylase and a gene encoding alcohol dehydrogenase, wherein said cell is *Saccharomyces cerevisiae* YPH499fps1Δgpd2Δ (pGcyaDakAdhPdc, pGupCas), wherein the accession number of *Saccharomyces cerevisiae* YPH499fps1Δgpd2Δ (pGcyaDakAdhPdc, pGupCas) is KCCM11152P.

2. A method for producing ethanol, comprising a step of culturing the cell of claim 1 using glycerol as a substrate.

3. A genetically engineered yeast cell, wherein the cell is *Saccharomyces cerevisiae* YPH499fps1Δgpd2Δ (pGcyaDak, pGup1Cas), wherein the accession number of *Saccharomyces cerevisiae* YPH499fps1Δgpd2Δ (pGcyaDak, pGup1 Cas) is KCCM11071P.

4. A method for producing ethanol, comprising a step of culturing the cell of claim 3 using glycerol as a substrate.

* * * * *

UNITED STATES PATENT AND TRADEMARK OFFICE
CERTIFICATE OF CORRECTION

| | | |
|---|---|---|
| PATENT NO. | : 8,772,000 B2 | Page 1 of 1 |
| APPLICATION NO. | : 13/641946 | |
| DATED | : July 8, 2014 | |
| INVENTOR(S) | : Sung Ok Han et al. | |

It is certified that error appears in the above-identified patent and that said Letters Patent is hereby corrected as shown below:

In the Specification

Column 2, line 53: "overexpresses TATA-binding" should be --overexpresses the TATA-binding--.

Column 6, line 24: "have fragment" should be --have a fragment--.

Column 6, line 30: "which used" should be --which is used--.

Column 8, line 66-67: "Hong-1-donor" should be --Hongje-1-dong--.

Column 9, line 61: "Building Hongje" should be --Building, Hongje--.

Column 9, line 62: "December 2010" should be --December 17, 2010--.

Column 13, line 47: ", pGupCas)." should be --, pGupCas)."--.

Column 16, line 4: "30° C." should be --30° C--.

Column 16, line 25: "30° C." should be --30° C--.

Column 16, line 45: "30° C." should be --30° C--.

Signed and Sealed this
Fourth Day of November, 2014

Michelle K. Lee
*Deputy Director of the United States Patent and Trademark Office*